United States Patent
Matt et al.

(10) Patent No.: US 11,901,080 B1
(45) Date of Patent: Feb. 13, 2024

(54) PREDICTIVE MODELING FOR USER CONDITION PREDICTION

(71) Applicants: Eric Matt, Aurora, CO (US); Andrew Carnes, Denver, CO (US); Jeffrey Cuthbert, Littleton, CO (US)

(72) Inventors: Eric Matt, Aurora, CO (US); Andrew Carnes, Denver, CO (US); Jeffrey Cuthbert, Littleton, CO (US)

(73) Assignee: C/HCA, INC., Nashville, TN (US)

(*) Notice: Subject to any disclaimer, the term of this patent is extended or adjusted under 35 U.S.C. 154(b) by 327 days.

(21) Appl. No.: 17/137,055

(22) Filed: Dec. 29, 2020

Related U.S. Application Data

(60) Provisional application No. 62/955,146, filed on Dec. 30, 2019.

(51) Int. Cl.
| | |
|---|---|
| *G16H 50/30* | (2018.01) |
| *G16H 10/60* | (2018.01) |
| *G16H 15/00* | (2018.01) |
| *G06T 7/00* | (2017.01) |
| *G06F 40/30* | (2020.01) |
| *G06F 18/214* | (2023.01) |
| *G06F 18/2411* | (2023.01) |
| *G06N 5/01* | (2023.01) |

(52) U.S. Cl.
CPC ........... *G16H 50/30* (2018.01); *G06F 18/214* (2023.01); *G06F 18/2411* (2023.01); *G06F 40/30* (2020.01); *G06N 5/01* (2023.01); *G06T 7/0012* (2013.01); *G16H 10/60* (2018.01); *G16H 15/00* (2018.01)

(58) Field of Classification Search
CPC ........ G16H 50/20; G16H 50/70; G16H 30/40; G16H 10/60; G16H 50/30
See application file for complete search history.

(56) References Cited

U.S. PATENT DOCUMENTS

| | | | | |
|---|---|---|---|---|
| 2015/0238270 | A1* | 8/2015 | Raffy | A61B 90/37 600/407 |
| 2022/0175325 | A1* | 6/2022 | Fukushima | G16H 50/30 |

FOREIGN PATENT DOCUMENTS

| | | | | |
|---|---|---|---|---|
| WO | WO-2021087317 | A1 * | 5/2021 | G16H 15/00 |

OTHER PUBLICATIONS

Gulshan, Varun, et al. "Development and validation of a deep learning algorithm for detection of diabetic retinopathy in retinal fundus photographs." Jama 316.22 (2016): 2402-2410. (Year: 2016).*

* cited by examiner

*Primary Examiner* — Devin C Hein
*Assistant Examiner* — Constantine Siozopoulos
(74) *Attorney, Agent, or Firm* — Kilpatrick Townsend & Stockton LLP

(57) ABSTRACT

Techniques are disclosed for determining a risk assessment corresponding to a level of risk that a user of a service organization has or will develop a condition. The techniques include receiving user data associated with a user record of a user. The techniques further include inputting the user data into a trained prediction model of a user condition prediction system. The user data may include a plurality of data points, weighted relative to each other, that respectively correspond to one of a plurality of categories. The techniques further include determining, by the trained prediction model, a risk assessment of a user condition based on the user data. The risk assessment may then be provided to a user device of a user service agent for use coordinating user service.

20 Claims, 25 Drawing Sheets

| Features | Importance | Features | Importance |
|---|---|---|---|
| Age | 1 | Min Glucose | 0.469 |
| Min Creatinine | 0.979 | Min Diastolic | 0.408 |
| Min Albumin | 0.918 | Ambulation | 0.408 |
| Min Hemoglobin | 0.857 | Incontinence | 0.387 |
| BMI | 0.795 | CRP Performed | 0.346 |
| Max Ensophil | 0.734 | Max CO2 | 0.326 |
| Temperature (C) | 0.734 | Sex | 0.306 |
| Blood Urea Nitrogen | 0.693 | Min Pulse | 0.265 |
| Max WBC | 0.693 | Min Triponin | 0.244 |
| Max Systolic | 0.632 | Avg Chloride | 0.163 |
| Avg Surg Proc Dur | 0.612 | Max ALT | 0.142 |
| Max Glucose | 0.53 | Max PulseOx | 0.061 |
| Min Bilirubin | 0.489 | | |

PREDICTIVE MODELING FOR USER CONDITION PREDICTION

CROSS-REFERENCE TO RELATED APPLICATION

This application claims the benefit of and priority to U.S. Provisional Application No. 62/955,146, filed Dec. 30, 2019, which is hereby incorporated by reference in its entirety for all purposes.

BACKGROUND

The amount of data generated each day continues to grow. In some environments, some of this data may be stored, while a majority of it may be evaluated and abandoned or ignored. Users and computing devices are beginning to rely more on this data to make decisions. This may be especially true when the data is introduced as part of an operational flow. However, the time required to sort through stored data can create inefficiencies and the fact that other data may typically be ignored or abandoned may create undesirable service results.

SUMMARY

Exemplary embodiments described herein provide techniques for providing a risk assessment that a user has or will develop a condition. In some embodiments, techniques are also provided for providing a recommendation for servicing the user based at least in part on the risk assessment. A prediction system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer-implemented method also includes receiving, by a prediction system, user data associated with a user record of a user of a unit, the user record being one of a plurality of user records maintained by a service management system of a service organization, the unit being one of a plurality of units affiliated with the service organization. The method also includes inputting, by the prediction system, the user data into a trained prediction model of the prediction system. The user data may include a plurality of data points that respectively correspond to one of a plurality of categories. The plurality of data points may be weighted relative to each other by the trained prediction model, and the trained prediction model may have been trained based at least in part on training data received from the service management system. The method also includes determining, by the trained prediction model, a risk assessment corresponding to a level of risk that the user has or will develop a condition. The method also includes providing, by the prediction system, the risk assessment to a user device of a user service agent for use in determining whether the user should receive a consult for the condition. Other embodiments of this aspect include corresponding computer systems, apparatus, and computer programs recorded on one or more computer storage devices, each configured to perform the actions of the methods.

Other objects, advantages, and novel features of the present invention will become apparent from the following detailed description of the invention when considered in conjunction with the accompanying drawings.

BRIEF DESCRIPTION OF THE DRAWINGS

Various examples in accordance with the present disclosure will be described with reference to the drawings, in which.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
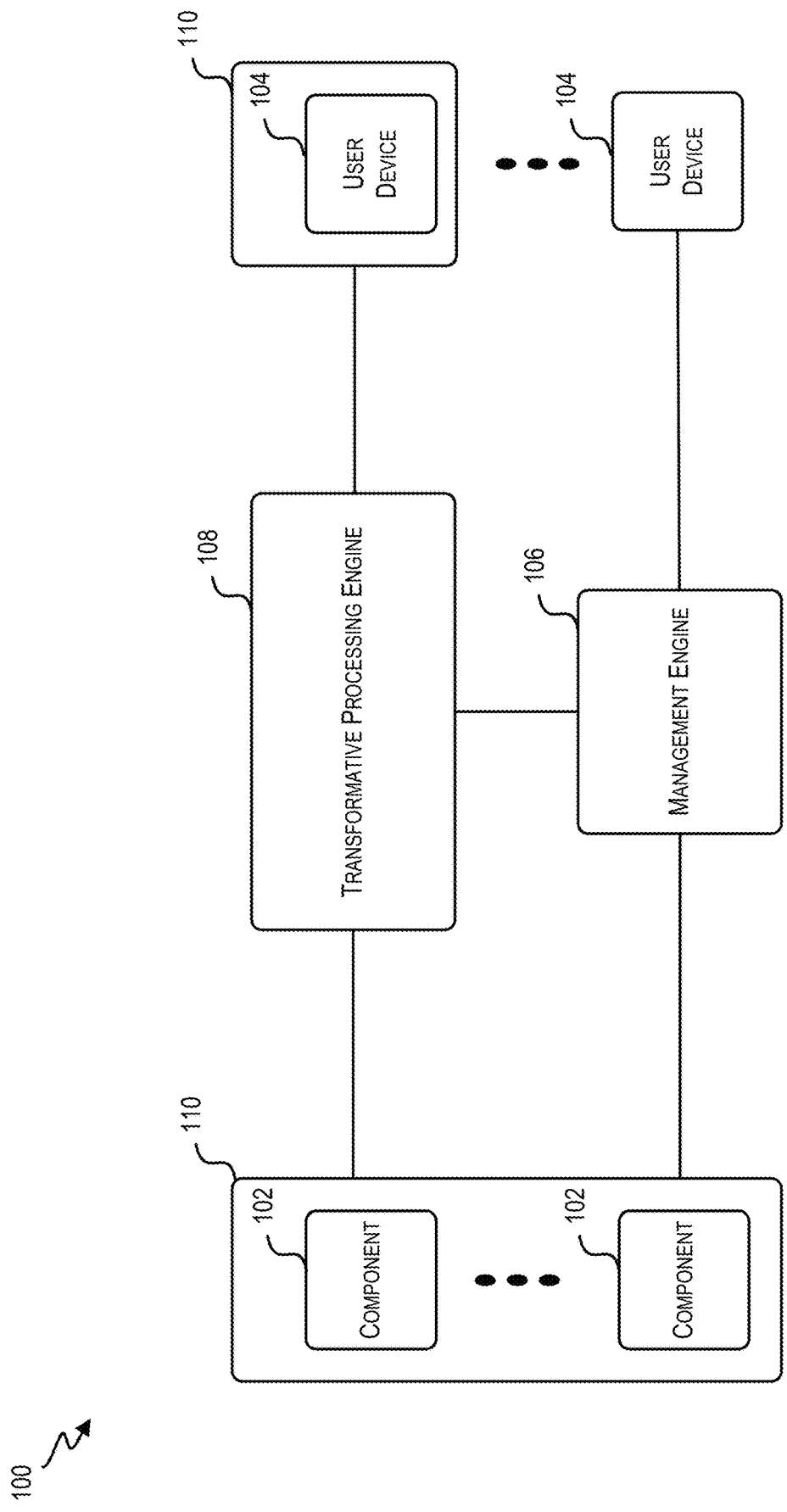
FIG. 1 is an example block diagram illustrating an interaction system in which techniques relating to providing a risk assessment that a user has or will develop a condition may be implemented, according to at least one example.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
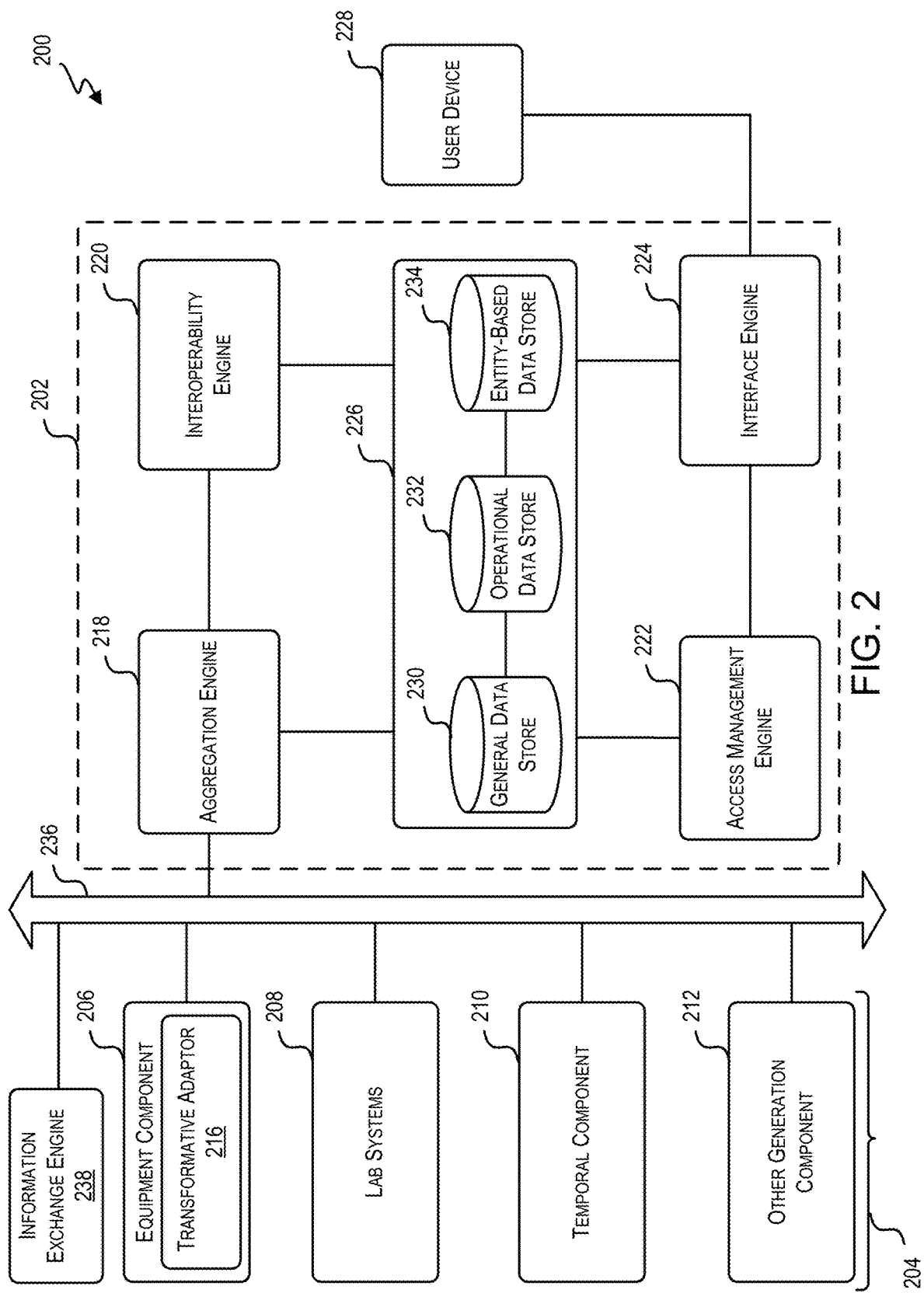
FIG. 2 is an example block diagram illustrating an interaction system in which techniques relating to providing a risk assessment that a user has or will develop a condition may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
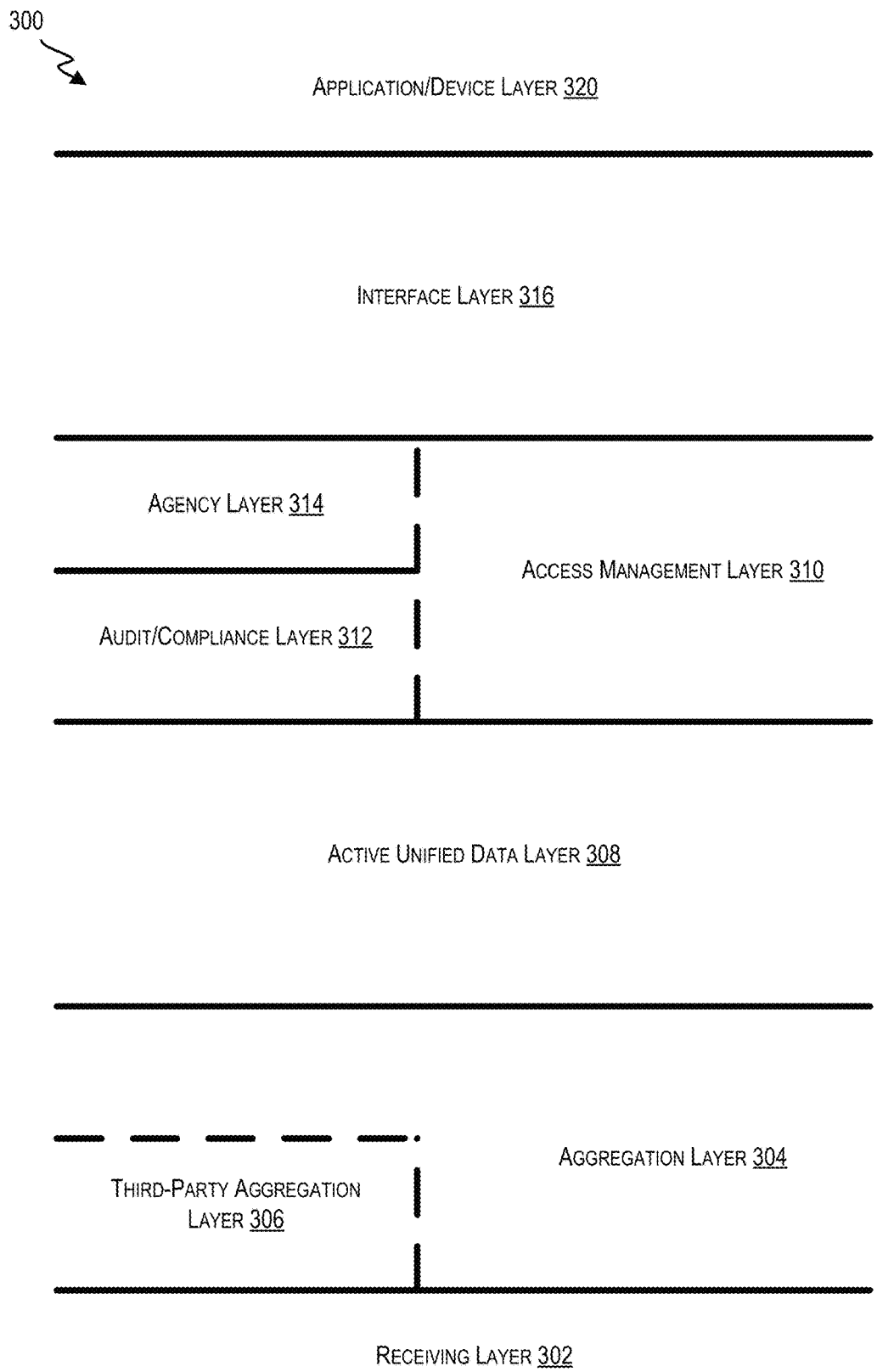
FIG. 3 is an example schematic model illustrating a network communication model in which techniques relating to providing a risk assessment that a user has or will develop a condition may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
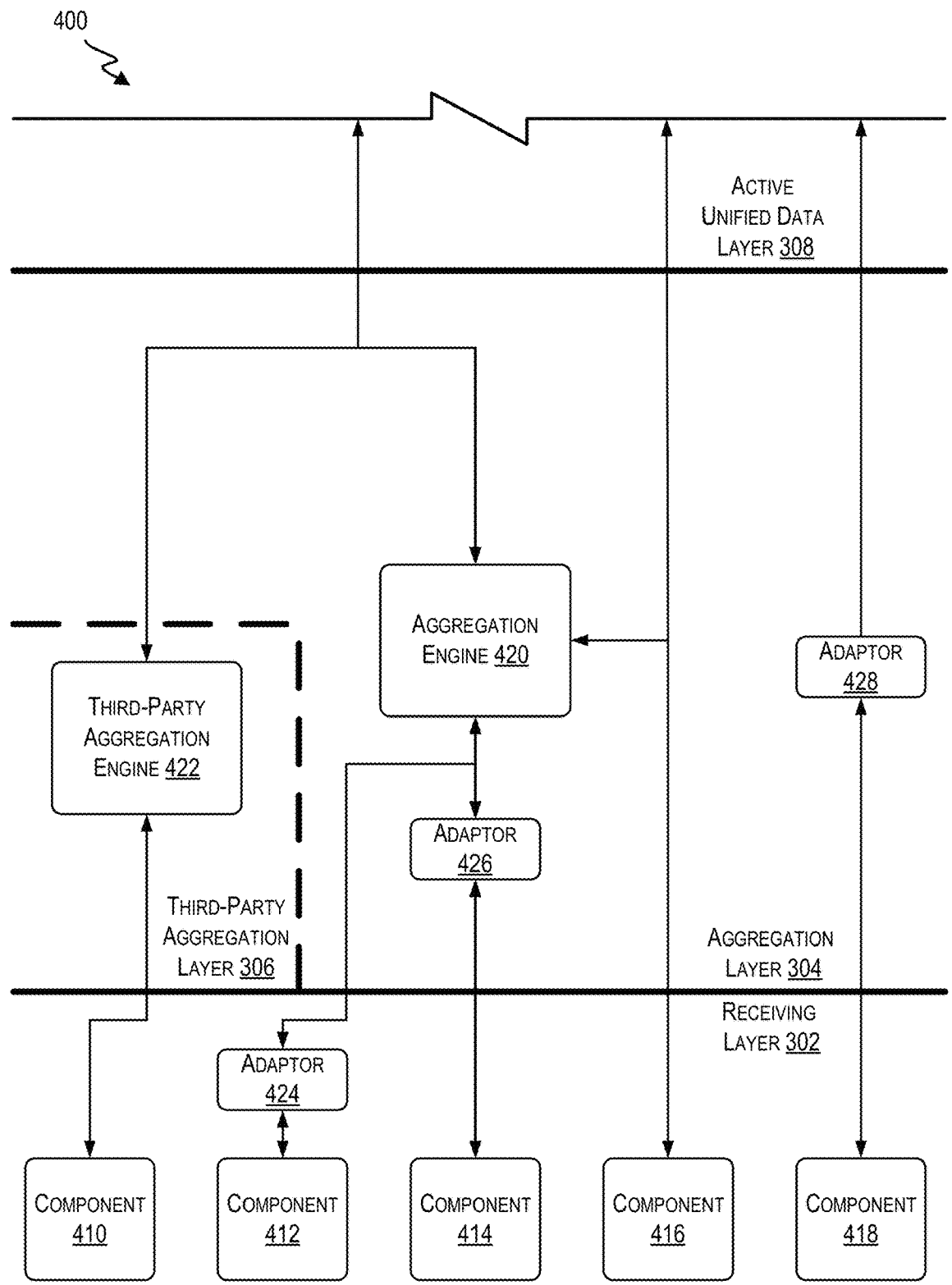
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
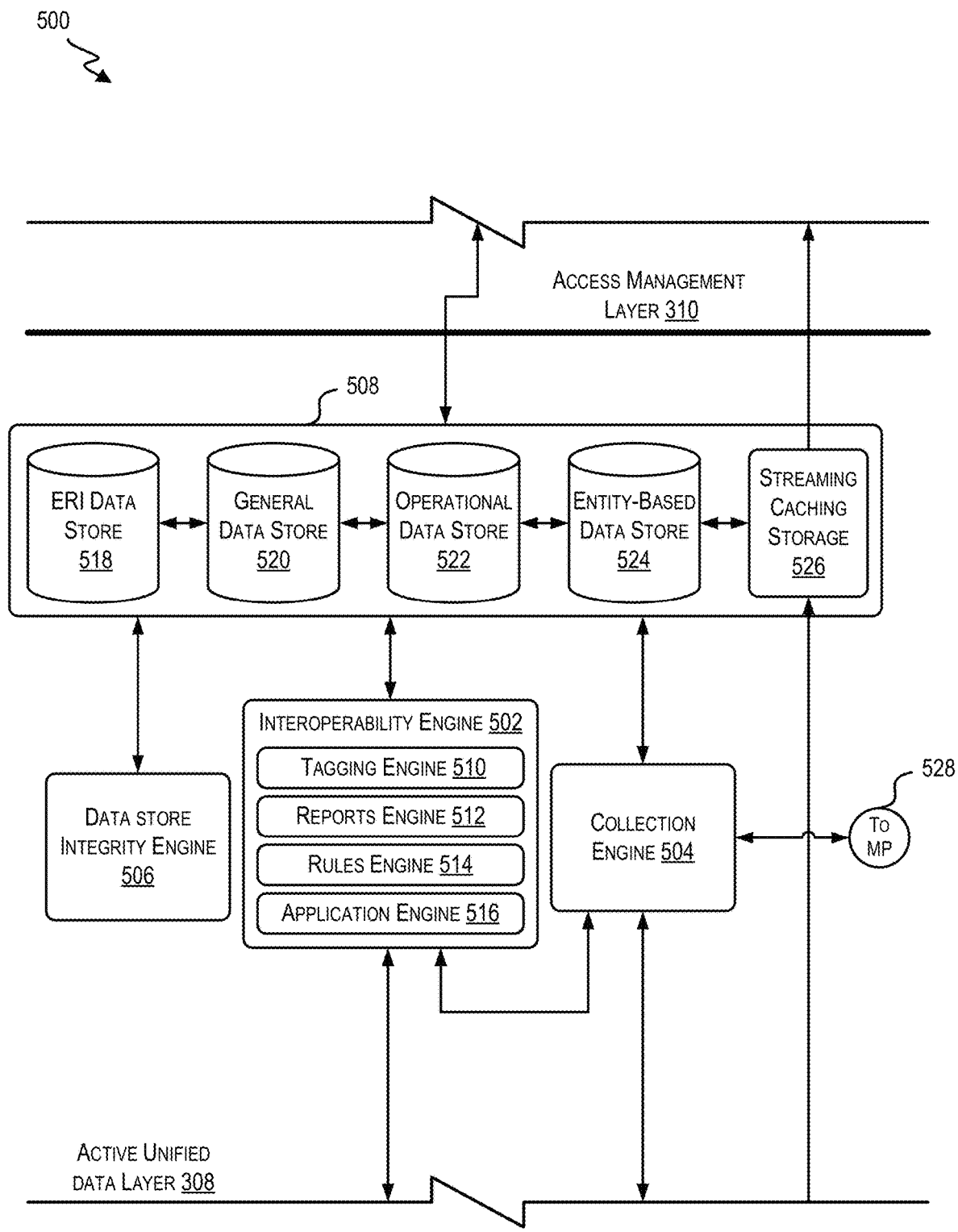
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
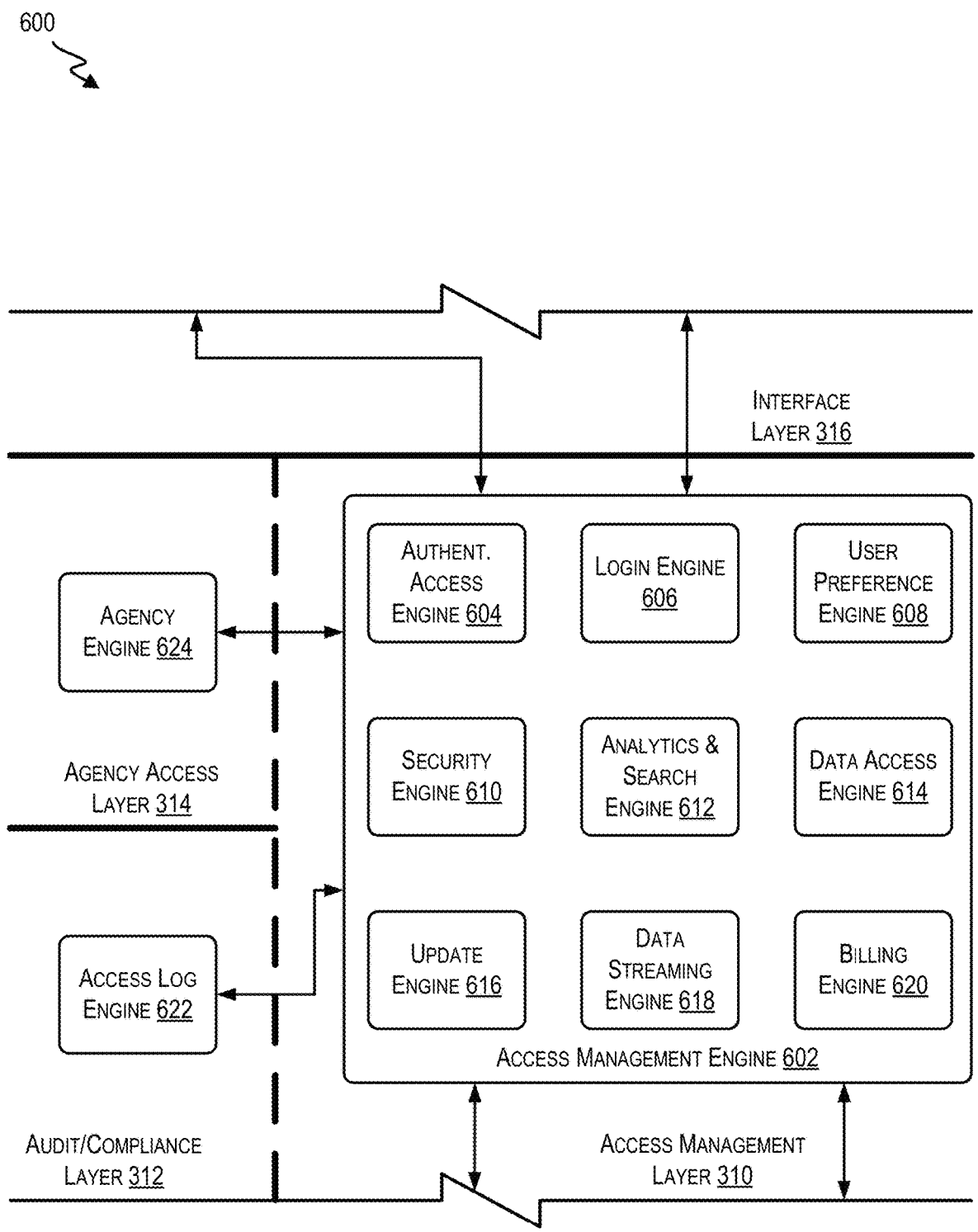
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user is able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
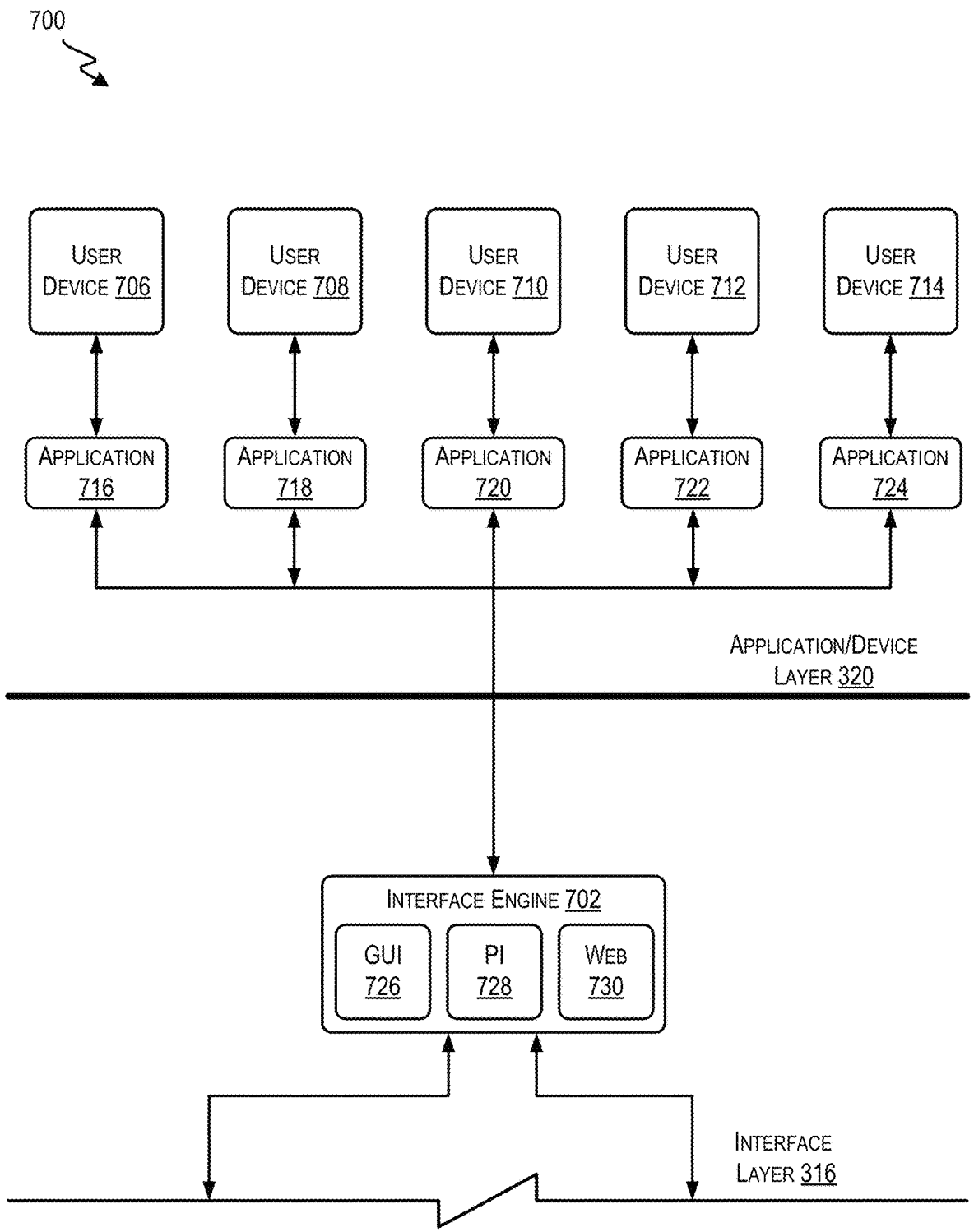
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data.

In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
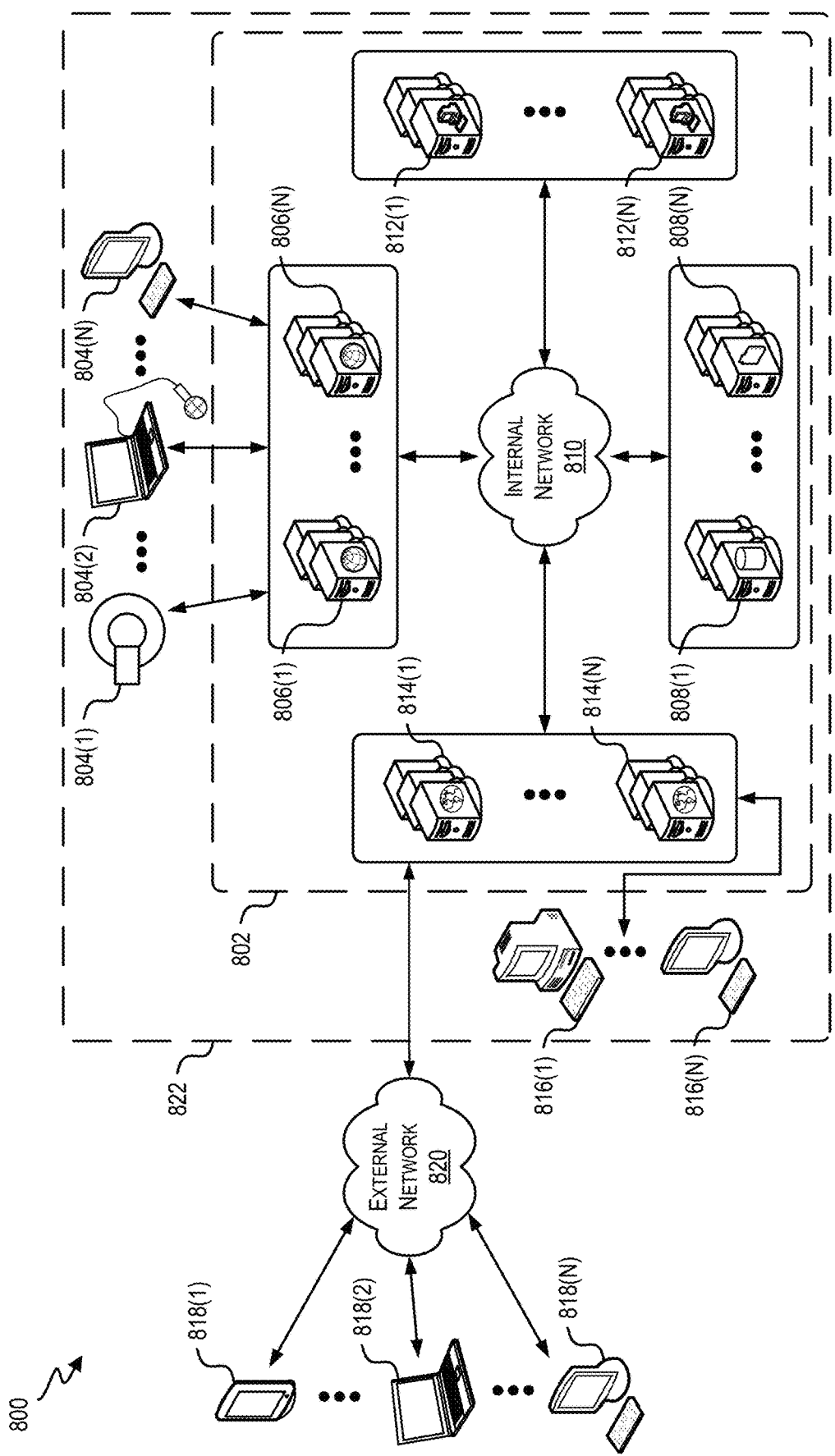
FIG. 8 is an example schematic architecture illustrating an interaction system in which techniques relating to providing a risk assessment that a user has or will develop a condition may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
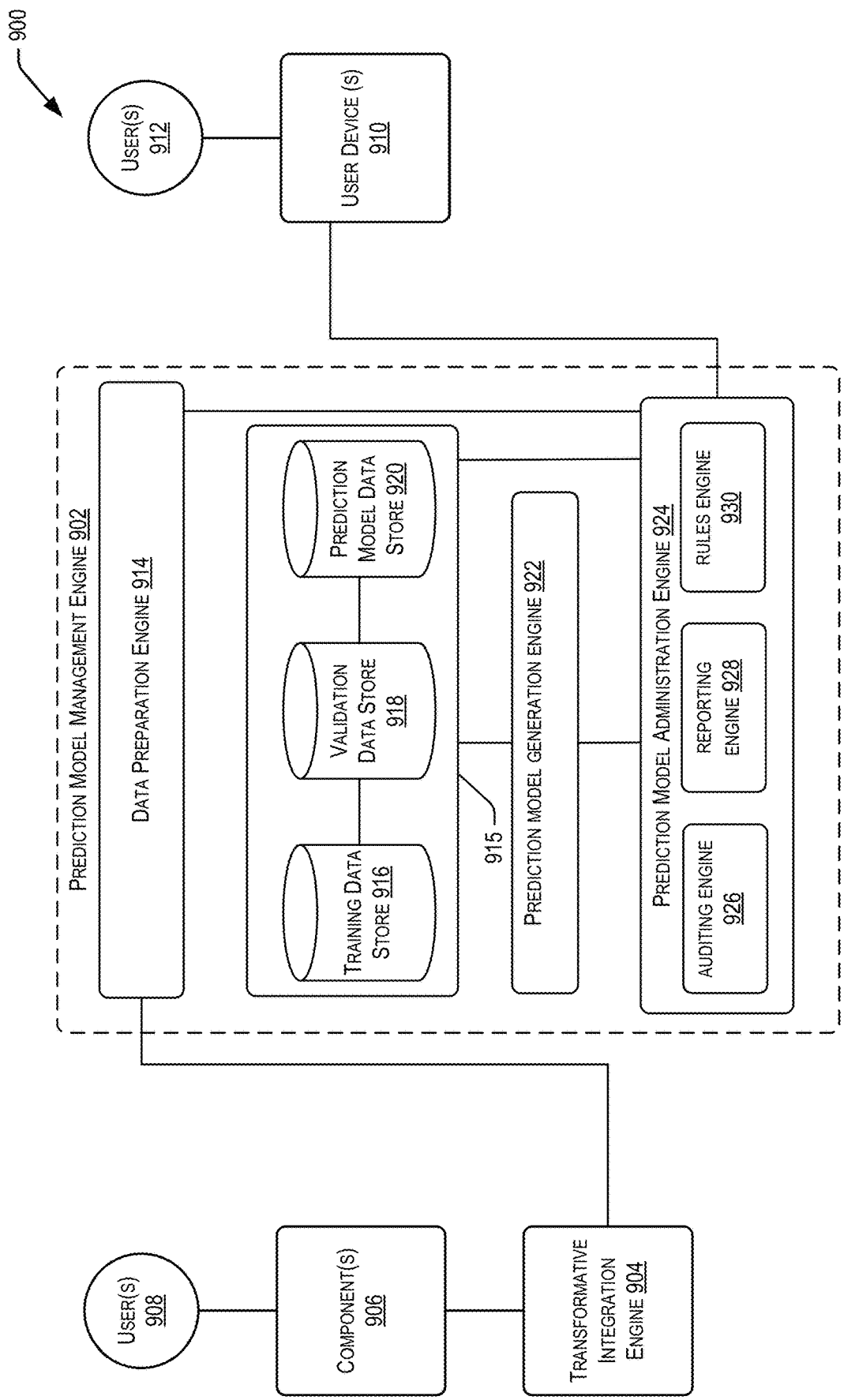
FIG. 9 is an example architecture illustrating a system in which techniques relating to providing a risk assessment that a user has or will develop a condition may be implemented, according to at least one example.

Turning now to FIG. 9, a block diagram of an example of a service provider prediction system 900 is shown. In some examples, the service provider prediction system 900 is a component of (or connected to) a service management system (e.g., a service provider network) that is affiliated with a service organization. The service organization may include one or more service (e.g., service) facilities, which may each transmit data to the service management system. The service management system may include one or more other components as described in FIGS. 1-8 described herein. The service provider prediction system 900 of FIG. 9 includes a prediction model management engine 902. The service provider prediction system 900 further includes a transformative integration engine 904. The transformative integration engine 904 is an example of the transformative integration engine 108 discussed with reference to FIG. 1. The service provider prediction system 900 also includes one or more generation components 906, which may be similar to the one or more generation components 204 discussed in reference to FIG. 2. In some examples, the generation components 906 may receive data input from one or more users 908 (e.g., clinicians, service technicians, etc.). The service provider prediction system 900 also includes one or more user devices 910 used by users 912 (e.g., user service providers (USPs) such as clinical nurse consultants). The user device(s) 910 may be similar to user device 228 of FIG. 2 and/or user device 104 of FIG. 1. The transformative integration engine 904 and the user device(s) 910 may communicate with the prediction model management engine 902 using any suitable network connectivity device, as described earlier.

In some examples, the transformative integration engine 904 may receive service-related data generated by the generation components 906 (e.g., a lab systems component 208, service equipment component 206, clinical component 212, etc.). The service-related data (e.g., lab results) may be collected from one or more service facilities of a service organization. The data can further include an identification of a user and/or other user-pertinent information (e.g., user service records, service history, genetic data, biometric data, actual or suspected diagnosis, and/or demographic information). The transformative integration engine 904 may receive the data in any suitable format and may transform the data into a format that is suitable for reception by the prediction model management engine 902. For example, the prediction model management engine 902 may access the transformed data via the interface engine 224 of the transformative integration engine 904. Data may be received by the prediction model management engine 902 using any suitable cadence (e.g., once a day, once an hour, once every minute, every few seconds, etc.). The data may be received (directly or indirectly) via either push or pull technology. In some examples, newly received data may be used to update (e.g., retrain) one or more prediction models of the prediction model management engine 902.

The prediction model management engine 902 includes a data preparation engine 914, a prediction model generation engine 922, a prediction model administration engine 924, and a data store 915. Generally, the data preparation engine 914 is configured to receive and process service-related data from the transformative integration engine 904. In some examples the data preparation engine 914 may prepare (e.g., further transform and/or segment) service-related data so that the data may be used to train and validate a prediction model. For example, a data set of service-related data may be split into different subsets by the data preparation engine 914. A training data subset may be generated that is used to train a particular prediction model (e.g., adjusting the weights between interconnected nodes of a neural network). In some examples, the same (or similar) training data subset may be used to train one or more prediction models utilizing different algorithms, and then a best model may be chosen. A cross-validation subset may also be generated that may be used to compare the performances of prediction algorithms that were created based on the training set. The cross-validation subset may be a separate set of data that is held back from training the model, and may be used to minimize over-fitting of data (e.g., verifying that any increase in accuracy achieved over the training data set is not due to over fitting). A test subset (e.g., separate from the training subset and cross-validation subset) may also be used to determine how a particular prediction algorithm will perform on new data. In some examples, any suitable segmenting of data received from the transformative integration engine 904 may be determined by the data preparation engine 914 for training a prediction model.

As discussed further herein, different types of algorithms (e.g., machine learning algorithms) may be used to generate prediction models. For example, the prediction model management engine 902 may perform supervised or unsupervised learning to generate prediction models. Typically, especially in the case of supervised learning, as part of the training and validation processes, ground truth labels may be created for data samples and included in (or alongside) one or more of the subsets of data determined by the data preparation engine 914. A ground truth label may refer to information that is provided by direct observation, as opposed to information provided by inference. The ground truth label may be used to measure the accuracy of a training data set's classification. For example, a prediction model may be trained to predict whether a user has a particular condition (e.g., cancer). A ground truth label for a particular user may be determined based on an actual observed outcome of the particular user's condition (e.g., a physician confirms that the user has cancer). The training sample for that user may include other data (e.g., blood analysis, biometric data, etc.), which may be used as input to train a prediction model. The prediction that is output by the prediction model may be compared against the ground truth label to determine the accuracy of the prediction, and the comparison results may be used to adjust (e.g., learn) weights and/or parameters of the model accordingly.

In some examples, the data preparation engine 914 may perform semantic tagging and indexing of service-related data (e.g., categorizing data). The data preparation engine 914 may also determine if gaps exist in the pool of data samples, whereby new data should be obtained to increase training coverage. For example, some users' service records may omit an attribute (e.g., Body Mass Index (BMI)) which may be determined to be an important feature for training a particular prediction model. In this case, the data preparation engine 914 may tag these records as requiring attention and transmit a notification to a user device of a system administrator for further action. The data preparation engine 914 may also perform feature engineering, which may involve further transforming and/or extracting the data into a different form that is suitable for training a particular prediction model. For example, the data preparation engine 914 may receive raw data corresponding to pixels of an image (e.g., of a portion of a user's body). The data preparation engine 914 may then perform one or more operations to analyze the pixels of the image to generate a new feature from the raw data (e.g., a level of skin redness). This new feature may then be used as one of the inputs to a machine learning algorithm (e.g., predicting a type of body condition). It should be understood that, in some cases, the data preparation engine 914 may execute a previously generated prediction model in order to engineer a feature that may in turn be used to train another prediction model.

From the data preparation engine 914, data may flow to the data store 915. The data store (and any other data store discussed herein) may include one or more data stores, which may be distributed throughout two or more different locations (e.g., present on different devices, which can include devices of different entities and/or a cloud server). In some examples, the data store 915 includes a training data store 916, a validation data store 918, and a prediction model data store 920. Within each of the data stores 916, 918, and 920 is stored prediction model-related data. In some examples, the structure of one or more of the data stores 916, 918, or 920 may be similar to data store 226. The training data store 916 may contain training data that is used to train a prediction model. The training data may include multiple samples (e.g., based on user service records), and may include ground truth data for each sample. Different sets of training data may be created from the multiple samples (e.g., generating a new training data set on a predetermined time interval). The different training data sets may also be training data subsets that are randomly generated from an overall pool of training data samples, so as to reduce the risk of overfitting. The validation data store 918 may contain training data that is used to validate a prediction model. For example, the validation data store 918 may contain cross-validation and/or test data subsets that are generated from the pool of training data samples. The training data stored in the validation data store 918 may be determined and further curated based at least in part on the composition of the training data sets in the training data store (e.g., generating disjoint sets of data for increased accuracy during validation and testing). The prediction model data store 920 may contain one or more prediction models, which may be either trained or untrained prediction models. The trained prediction models may be generated from the prediction model generation engine 922, discussed further below. The prediction model data store 920 may further include parameters that may be used to train (or update) a prediction model. As a non-limiting example, this may include a type of loss function, a learning rate (e.g., how much to adjust data weights after each training iteration), a subsample size (e.g., indicating how many training samples should be used to train a new model), a number of nodes (e.g., in the case of a neural network), a number of leaves/levels (e.g., in the case of a decision tree), a number of trees (e.g., in the case of a boosted decision tree model), etc.

The prediction model generation engine 922 is configured to generate one or more trained prediction models based at least in part on data from the data store 915. A trained prediction model may be trained to identify which set of one or more categories a new observation (e.g., data from a user's service record) belongs. In the case of supervised learning, this may be based on the training set of data containing observations whose category membership is known (e.g., a user who is known to have a particular cancer, which observation may be recorded as a ground truth label). In the case of unsupervised learning, this may be based on grouping data into categories based on some measure of inherent similarity or distance (e.g., clustering). In either type of learning, a trained prediction model may classify an observation as a binary classification (e.g., patent has or does not have a condition) or a multiclass classification (e.g., user has a particular type condition of several possible condition types). In some examples, a trained prediction model may use observation data to output one or more classifications (e.g., assessments) about one or more respective aspects regarding a user's condition (e.g., a likelihood of a condition, a type of condition, a severity of condition, etc.). Each of these one or more classifications may be either binary or multiclass classifications. The classifications may include one or more values (e.g., a binary value, or a real number (between 0-1)) that indicate a likelihood of a particular classification being an accurate assessment.

The prediction model generation engine 922 may utilize one or more artificial intelligence techniques to generate a prediction model. As used herein, the term "artificial intelligence" (AI) refers to any suitable computer-implemented artificial intelligence technique including, but not limited to, machine learning (ML) (supervised or unsupervised), natural language processing, machine perception, computer vision, affective computing, statistical learning and classification, Bayesian network models and Kalman filters, reinforcement learning including neural networks, search algorithms and optimization algorithms (including evolutionary computing) and automated reasoning. Non-limiting examples of classification algorithms include use of hidden Markov models, decision trees (e.g., boosting decision trees, random forests), support vector machines, etc.

The prediction model administration engine 924 may be utilized to configure the prediction model management engine 902. In some examples, the prediction model administration engine 924 includes an auditing engine 926, a reporting engine 928, and a rules engine 930. The auditing engine 926 may include elements for tracking and monitoring the performance of a prediction model. For example, the auditing engine 926 may be configured (e.g., by a user device 910) to monitor precision and recall values (and/or sensitivity and specificity values) for a prediction model over time, as new data is received and input into the prediction model. The reporting engine 928 may include elements for generating one or more reports that are consumable by a user 912 via a user device 910. For example, the reporting engine 928 may execute one or more trained prediction models to generate a report for a one or more users. The report may indicate, for each user, a predicted classification of the user based on current user data (e.g., whether the user has a particular condition or not). The report may include other information (e.g., user demographics, user admission data, etc.), which may assist a user service coordinator in determining a course of service for the user. The reports engine 928 may also output reports on a periodic basis that indicate the performance of one or more prediction models, which may be used to determine whether a model should be retrained with updated data. The rules engine 930 may determine one or more rules for managing aspects of the prediction model management engine. For example, the rules engine 930 may receive input from a user device 910 that is used to configure the data preparation engine (e.g., add a new feature to the list of predictive features being tagged). The rules engine 930 may also be used to configure aspects of the data store 915 (e.g., controls for determining which data should be grouped into a training subset versus a test and/or cross-validation subset, how large a training sample subset should be, etc.). The rules engine 930 may also be used to configure aspects of the prediction model generation engine 922. For example, the rules engine 930 may receive input indicating when a new prediction model should be generated (e.g., on a predetermined cadence, using one or more ML algorithms with particular parameters, etc.).

Figure 10:
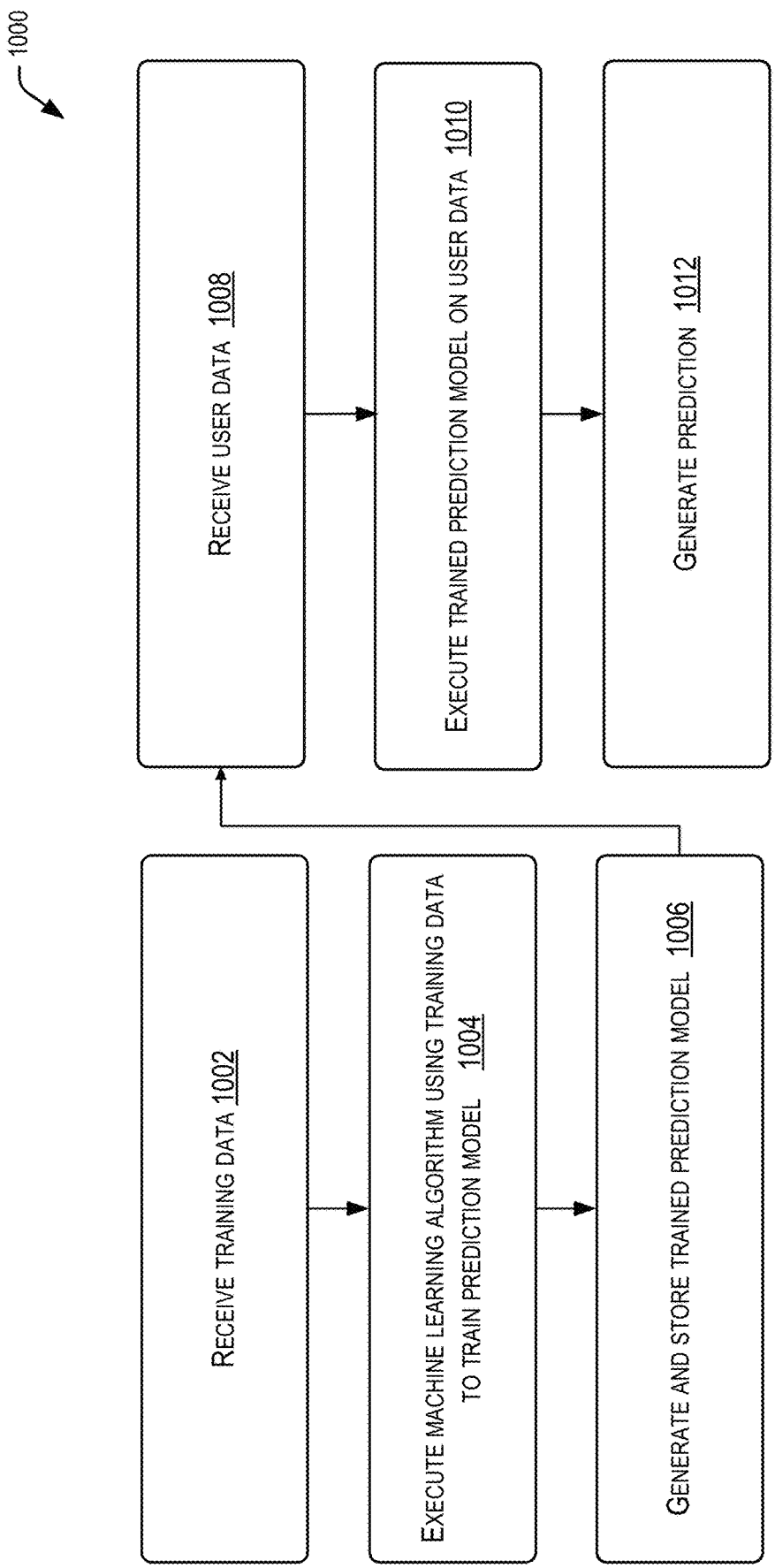
FIG. 10 is an example flowchart illustrating a process for providing a risk assessment that a user has or will develop a condition, according to at least one example.

Turning to FIG. 10, an example flow diagram 1000 is depicted for a computer system training a prediction model and executing the trained prediction model. The flow diagram may proceed in two phases: a training phase (blocks 1002-1006) and an execution phase that follows the training phase (blocks 1008-1012). In some examples, the computer system that performs the process 1000 may correspond to the service provider prediction system 900 of FIG. 9.

Some or all of the flow 1000 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Additionally, these processes are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

The example flow 1000 may start at block 1002, whereby the system may receive training data. In some examples, the training data may be generated from one or more generation components 204 (e.g., lab systems, clinical components, etc.). In some examples, the one or more generation components 204 may belong to different service providers (e.g., different service facilities) within a service organization. In some examples, the training data may be received from other sources outside the service organization (e.g., third party entities, government organizations). The training data may be associated with and/or derived from user data of users, for example, derived from user electronic service records. In some examples, a training data sample of the training data may include a plurality of data points that identify characteristics of a user, diagnoses made by service providers, associated service plans for the user made by the providers, associated outcomes of the user based on those service plans, condition indicators for the user, laboratory test results (e.g., from blood, urine, and/or other tests), and other suitable information. In some examples, the training data may indicate not only historical service data, corresponding to previous admissions of the user, but may also include present admission data, corresponding to a present admission of the user for a condition. The user data may be received in any suitable form, including, but not limited to, text, audio, video, digital images, and numerical values. The training data may be processed and/or transformed into a suitable form for training a prediction model, for example, by data preparation engine 914. In some examples, this may involve semantically tagging the data, segmenting the data into different subsets (e.g., training sets, cross-validation subsets, testing subsets, etc.), performing feature engineering to generate one or more features for training the prediction model, etc. The training data may be stored in a data store (e.g., data store 915) for future use in training a prediction model.

At block 1004, the system may execute a machine learning algorithm using the training data to train a prediction model. Any suitable machine learning algorithm may be used to train the prediction model, including supervised learning algorithms (e.g., logistic regressions, neural networks), unsupervised learning algorithms (e.g., K-means, Apriori algorithm), and/or reinforcement learning algorithms (e.g., Markov decision processes).

In a first non-limiting example of a supervised learning algorithm, a neural network machine learning algorithm may be used to generate a prediction model using a set of inputs (e.g., training data) that includes one or more features, which in some cases may be measurable properties derived from user data (e.g., blood cell count, blood pressure, age, etc.). Any suitable number of features may be used as input to generate the prediction model. Using this technique, the set of inputs may be used as an input layer and the set of outputs may be used as an output layer. In this technique, the input layer may be connected to the output layer via one or more hidden layers. Each layer may include a set of one or more nodes, whereby each node may represent a piece of information. The generated prediction model may include a number of interconnections between the hidden layers and the input layer and/or output layer (e.g., between nodes of the different layers), each of which may be assigned a numeric weight generated based on a pattern identified between the set of input values and the set of output values. The weight may be tuned (e.g., based on a training dataset), rendering the artificial neural network adaptive to inputs and capable of learning. Generally, the hidden layer(s) allows knowledge about the input nodes of the input layer to be shared among the output nodes of the output layer. To do so, a transformation f is applied to the input nodes through the hidden layer. The artificial neural network may also use a cost function to find an optimal solution (e.g., an optimal transformation function). The optimal solution represents the situation where no solution has a cost less than the cost of the optimal solution. In an example, the cost function includes a mean-squared error function that minimizes the average squared error between an output f(x) (e.g., a prediction, given training data input x) and a target value y (e.g., a ground truth value) over the example pairs (x, y). In some examples, a backpropagation algorithm that uses gradient descent to minimize the cost function may be used to train the artificial neural network. In this example, one or more parameters (e.g., which also may be known as "hyperparameters") may be used to administer the training process. For example, these parameters may include determining how many hidden layers of nodes to use between the input layer and the output layer, and how many nodes each layer should use. In this example, the collection of nodes and determined weights (e.g., based on training data) between interconnections of nodes between the different layers may comprise the trained model. Once the artificial neural network (i.e., prediction model) has been generated, it may be used to predict one or more events (e.g., regarding a user's present and/or future condition) upon receiving input (e.g. user data).

In a second non-limiting example, a boosted decision tree technique may be used to generate a prediction model using a set of inputs (e.g., training data) that includes one or more features. Each feature may directly correspond a data point (e.g., BMI, blood pressure, etc.), or be derived from one or more data points, similar to as described earlier. This technique is also a supervised learning method and may utilize a labeled dataset with ground truth data. A pre-trained decision tree may receive a set of input features as input and then split the input data based on those features. For example, a given node in a decision tree may split (e.g., determine an outcome) based on the respective values of one or more input features input to the given node. The selection at each node of what is the next best feature to split on may be performed based at least in part on determining which features maximize information gain and/or to minimize entropy, and may be chosen as part of a (e.g., recursive) learning/training process used to generate the decision tree. The process may be repeated until a stop condition is met (e.g., the process reaches the depth of the tree, no more information gain, etc.). Terminal nodes of the decision tree may represent a class label (e.g., the user has a particular type/stage of condition) or probability (e.g., probability that a user has a condition), which may correspond to a prediction outcome. In some examples, the outcome may be a continuous variable.

Using a boosted decision tree technique, multiple weak learners (e.g., an ensemble of decision trees) may be combined into a strong classifier. In some examples, each new decision tree may be created iteratively with respect to a distribution (e.g., associated with ground truth data from a training data set), and new trees may be generated based at least in part on previous trees. On each iteration, the new tree's prediction from a data sample may be given a weight relative to its accuracy. In some examples, the ensemble output (from the multiple trees) may be a weighted sum that may be compared against the ground truth. Additionally, after each iteration, each data sample (e.g., including one or more features from the data sample) may also be given a weight based the decision tree's misclassification. In this way, the more often a data sample is misclassified, the more important the data sample (and/or individual features of the data sample) becomes. The process of training the ensemble of decision trees that collectively predict an outcome (i.e., "boosting") may also include minimizing a cost function, which, similar to above, may include a function that measures the distance between the ground truth (y) and an output f(x) (e.g., to minimize the mean-squared error).

Based at least in part on the relative weight of the output of each decision tree in an ensemble and/or the relative weights of data samples, the system may be able to determine a relative importance of features among the set of features that are represented in the ensemble of decision trees (e.g., represented by the positioning of each node within a respective decision tree and the splitting behavior assigned to the node). In some examples, the relative importance among features may represent which feature is likely to result in the most information gain among other features. The system may also be able to determine, based at least in part on the splits determined for each node in the ensemble of trees, classifier decision boundaries. A classifier decision boundary is a decision boundary that partitions an underlying vector space into two sets (e.g., user has the condition, or the user does not have the condition). In some examples, a classifier decision boundary may be determined by an ensemble of classifiers (e.g., a boosted decision tree model) based at least in part on respective values (e.g., a range of values) for one or more features of the plurality of features that are input into the model. In a simplified example, one feature may be age, and another feature may be BMI of a user. For a particular condition, the model may determine that for an age range of 60 years old or more, and a BMI range 15-17, a user would be classified as having a particular condition. In some examples, multiple classifier decision boundaries may be determined from a boosted decision tree model, which may be collectively used as input to determine a final prediction. For example, one classifier decision boundary may determine, from one set of features, that the user is likely to have a condition with a first probability. Another classifier decision boundary may determine, from another set of features, that the user is likely to have (or not have) the condition with a second probability. The first and second probabilities may be combined together to determine a final probability (e.g., prediction). In some examples, this combining process may be represented within the trained boosted decision tree model using ensemble modeling. Similar to the neural network example, one or more parameters may be used to administer the training process. For example, these parameters may include determining a maximum depth of a tree, a maximum number of leaves, a maximum number of features (e.g., from the full set of features) that may be used to build a given tree, a minimum number of samples required to make a new leaf, etc.). Once the (boosted) decision tree prediction model has been generated, it may be used to predict one or more events (e.g., regarding a user's present and/or future condition).

While two possible examples of prediction models were mentioned above, it should be understood that any suitable prediction model may be utilized. Typically, the system will receive training data (e.g., user data received from the service organization) that is used to train the prediction model by learning characteristics (e.g., patterns and/or relationships) from the training data and thereby determining properties (e.g., weights) of the model. The system may also determine one or more parameters that may be used in training the model, whereby the parameters may be determined based on the type (e.g., structure) of model chosen (e.g., neural network, decision tree, linear regression, naive Bayes, etc.). In some examples, one or more prediction models may be chained together using an ensemble modeling to obtain better predictive performance. Additionally, in some examples, the output of one prediction model may be used as an input (e.g., as a feature) to another predictive model. For example, a first prediction model may be a neural network that predicts and/or classifies a type of skin condition. The output of the first prediction model may be used as a feature input to a second prediction model (e.g., a boosted decision tree model) that may predict a particular stage of the skin condition (e.g., injury) with a certain probability.

At block 1006, the system may generate and store the trained prediction model 1006. The generated prediction model may include any suitable data structures utilized from block 1004 to train the prediction model, as well as learned information during the training process (e.g., a meaning assigned to a node, a position of the node within the model, a weight value for a node, etc.). In some examples, the parameters used to train the given prediction model may also be stored, for example, to be later used in updating the model. For example, the prediction model administration engine 924 may perform an audit of the prediction model, and, based on the results of the audit, determine that one or more parameters used to train the model should be adjusted (e.g., increasing the maximum number of leaves). The trained prediction model may be stored in the prediction model store 920.

At block 1008, at a later time following the generation/storage of the prediction model at block 1006, the system may receive user data for use in generating a prediction about a user. In some examples, the user data may correspond to current information about a particular user (e.g., service records for a present admission to a service facility). Similar to the training data, the user data may also include a plurality of data points that identify characteristics of the particular user. In this case, however, instead of the data being used to train a prediction model, it will be used as input into the already-trained prediction model for use in generating a prediction about the condition of the user (e.g., for the present admission). In some examples, one or more of the plurality of data points of the user data may correspond to (and/or be used to derive) features by which the prediction model was trained to make predictions.

At block 1010, the system may execute the trained prediction model on the received user data. As described earlier, the system may use the user data for the particular user to extract features that are used as input to the prediction model (e.g., to an input layer of a neural network, root node of a decision tree, etc.).

At block 1012, the system execute the trained prediction model to generate a prediction about the user. The prediction may correspond to an assessment about a present condition or potential future condition of the user. In some examples, the assessment may include data associated with a plurality of conditions of the user (e.g., multiple conditions on the body). In the case where the prediction corresponds to an assessment about a present condition, the prediction may indicate a likelihood that the user has a particular present condition. In the case where the prediction corresponds to an assessment about a potential future condition, the prediction may indicate a likelihood that the user will develop the potential future condition. As a non-limiting example, a potential future condition may correspond to the existence an illness affecting the user, a severity and/or stage of the illness, a likelihood that another related illness or condition may develop, etc. In some examples, the prediction may correspond to a probability score (e.g., between 0-1). In some examples, the prediction may correspond to a classification of a likely group to which the user belongs (e.g., Stage 1, Stage 2, Stage 3, etc.). For example, the prediction may include a plurality of probabilities that respectively correspond to a likelihood of the user's illness being at a particular stage (e.g., Stage 1=0.23, Stage 2=0.64, Stage 3=0.13). As referenced herein, depending on the context, a "prediction" may be used interchangeably with a "probability score" or "risk assessment." In some examples, the prediction may be classified based on whether or not a probability score included within the prediction matches (e.g., equals or exceeds) a predefined threshold value. For example, a user with a probability score of at least 80% may be deemed to be "High Risk." This classification based at least in part on the predefined threshold value may be built into the trained prediction model (e.g., part of the training process), or may be a separate computation that follows the prediction model outputting one or more scores.

The systems, processes, and models described with reference to FIGS. 1-10 may be used to implement the techniques described herein with reference to later figures. For example, data communication may be performed within the aggregation layer 304 or the active unified data layer 308. In some examples, messages originate at one of the components 410-418 (e.g., generation components 204) and are streamed to the data store 508. These messages may be intercepted by the collection engine 504 or any other suitable interceptor device and shared with the prediction system described herein. Exemplary embodiments described herein provide techniques for providing a risk assessment that a user has or will develop a condition. In some embodiments, techniques are also provided for providing a recommendation for servicing the user based at least in part on the risk assessment.

In one example, a prediction system provides support for a user service provider (USP) that is providing service for users within a service organization (which may also be known as a "service system" or "enterprise"). The enterprise may include a plurality of divisions, and each division may include one or more service facilities. For example, the enterprise may geographically organized within the United States (U.S.), whereby there is a division per state, county, or the like. Each division may include one or more service facilities, for example, including service units, labs, rehabilitation centers, home service agencies, and any other user service center where a user may receive service by a service provider. The service organization may maintain a service management computer system, which coordinates user service and records across the service organization (e.g., via an Electronic Medical Record (EMR) system). In some examples, the service management system may further include (or be associated with) the prediction system. In some cases, the USP may be an administrator of the enterprise (e.g., at an enterprise level, division level, or service facility level). In some cases, the USP may be a service provider such as clinical nurse consultant (CNC), a floor nurse, a specialty nurse, a physician, or other service professional.

Typically, a service facility will admit a user for one or more conditions, and the user may receive service for the one or more conditions for a period of time, after which time the user is discharged. One of the conditions may be a type of pressure injury. A pressure injury (PI) (which may also be known as a "pressure ulcer") may be a localized injury to the skin and/or underlying tissue. A pressure injury may be a result of pressure or shear to the skin (often over a bony prominence), and may further be associated with other factors (e.g., age, immobility, nutritional status, hematological measures, illness severity, etc.). In some cases, the user may have initially developed the pressure injury outside the service facility, which may be known as a community-acquired pressure injury (CAPI). For example, the user may be a bedridden, chair bound, or otherwise immobile person, and may have developed a pressure injury at home due at least in part to prolonged pressure on the skin. In some cases, the user may initially not have any pressure injury (or the pressure injury may be latent), and may be admitted for a particular condition that is unrelated to the existence of a pressure injury. However, over time, the user may develop a hospital-acquired pressure injury (HAPI), for example, after a stay for service in a service unit (e.g., a hospital) which involved a significant period of time of being immobile. A service facility may desire to determine, as early as possible, whether an admitted user has a pressure injury (or is likely to develop a pressure injury) so that a USP may provide better service to the user. To help coordinate service among service facilities of the enterprise, improve user outcomes, and improve efficiencies of providing user service, the prediction system may provide support to a USP in several different forms and using various methods. For example, the prediction system may provide a risk assessment (e.g., a "wound assessment") to a user device of a USP that corresponds to a level of risk that the user has or will develop a pressure injury. In some examples, the risk assessment may include a probability score (e.g., between 0-1) that predicts the likelihood that the user has or will develop a pressure injury. In some examples, the risk assessment may be determined with respect to a predetermine time interval. For example, the risk assessment may correspond to a level a risk that the user will develop a pressure injury within a certain number of days, which may correspond to a typical length of stay at a service facility for a user with the particular condition of the user. In some cases, the risk assessment may include a prediction that is based in part on a probability score matching (e.g., equaling or exceeding) a threshold value. For example, the risk assessment may indicate a "High Risk" if the probability score is greater than or equal to the threshold value (e.g., 80%), a "Medium risk" if the probability score is between 50-79%, and a "Low risk" if the probability score is less than 50%. In some cases, the risk assessment may further include a recommendation for service based on the predicted level of risk of a pressure injury existing or developing. For example, a user with a high risk for a pressure injury may be determined to be a strong candidate for receiving a wound consult. A wound consult may include a physical examination of the user by a USP (e.g., a specialty wound nurse) to determine appropriate special service for the user that may be desired, given the risk of a pressure injury (e.g., a service bed that helps to mobilize the user).

In some examples, the prediction system may generate a risk assessment by utilizing a prediction model. The prediction model may be a classifier that utilizes one or more machine learning techniques. In a non-limiting example, a prediction model of the prediction system may utilize a boosting technique that is applied to an ensemble of decision trees, as discussed further herein. It should be understood that any suitable prediction model generation technique may be utilized to perform examples of the present disclosure. The prediction model may be trained based on training data including a plurality of training data samples received from one or more facilities of the enterprise. In some examples, a training data sample may be based on a user service record and may include a plurality of data points. For example, some of these data points may correspond to a user's age, ambulation, incontinence, body temperature, etc. The plurality of data points may be used to derive one or more training features, whereby each training feature may be determined based in part on its ability to predict a likelihood that the user has or will develop a pressure injury. In some examples, each of the plurality of data points (e.g., features) may be used to train the prediction model, for example, being used to determine parameters for nodes of the prediction model. Each feature may respectively correspond to one of a plurality of categories. As a non-limiting example, the plurality of categories may include age, body mass index (BMI), blood quality of the user, heart quality of the user, body healing indicators, user admission data, etc. In some examples, as a product of the training process, each of the plurality of data points may be weighted and/or ranked relative to each other in terms of importance (e.g., predictive value) in generating the risk assessment. The prediction model may be also be used to determine one or more classifier decision boundaries (e.g., between two or more of the data points), which may be used individually or collectively to generate a risk assessment. Once the prediction model has been trained, the trained prediction model may receive as input data elements from an admitted user's service record, and output a risk assessment. The risk assessment may then be displayed on a user device of the USP, to be used to determine appropriate service. The prediction model may be configured to run at a predetermined time interval (e.g., multiple times per day). For example, each run may include the prediction model receiving, as input, new and/or updated user data for users presently admitted to a service facility (or division, enterprise, etc.), and then outputting risk assessments for each user. In this way, each new run may account for users recently admitted and updated statuses (e.g., new blood test results) for each user. Accordingly, the risk score for a given user may change over time, and a USP may be able to track the changes and take appropriate action.

To provide a higher rate of predictive accuracy for a given risk assessment output by a prediction model of the prediction system, a prediction model may be trained using training data drawn from user samples drawn from across the enterprise. In one example, a first prediction model may be trained using training data from user records from each service facility in the enterprise. This may provide a broad sampling of training data to achieve a desired balance between bias error and variance (e.g., reducing overfitting and/or underfitting of data), and to improve specificity and sensitivity statistics. Meanwhile, a second prediction model may be trained using only a portion of the user service records of the enterprise (e.g., focusing on a particular division, or department). By training the second prediction model using only training data from the subset of user records, the second prediction model may be better configured to predict user outcomes for users in that specific geographic region (or department). In some examples, the first prediction model and the second prediction model may be combined together using one or more mechanisms. For example, the output of the first prediction model may be used as an input to the second prediction model, or vice versa. In another example, both prediction models may each output a respective risk assessment (e.g., including respective probability scores), and then the respective probability scores may be combined according to an algorithm (e.g., using ensemble modeling). It should be understood that the use of multiple prediction models may be employed at various levels within the enterprise (e.g., per division, per service facility level, per department, etc.). The two or more prediction models may be combined using any suitable mechanism, for example, as described above. By training a prediction model at a lower (e.g., per service facility) level, the prediction model may be better attuned to characteristics (e.g., user demographics, clinical data, financial data, geographical considerations) of a particular service facility.

In another example, a prediction model of the prediction system may assist a USP by predicting a particular stage of a pressure injury. For clarity of illustration, typically, a pressure injury may be classified into one of four possible stages. A stage one pressure injury may correspond to sores that are not open wounds. The sore may present as intact skin with non-blanchable redness of a localized area, usually over a bony prominence. The area of the injury may be more painful, firm/soft, warmer/cooler than adjacent tissue. A stage two pressure injury may correspond to a partial thickness loss of dermis that presents as a shallow open ulcer with a red/pink wound bed, without a sloughing of the skin. The stage two injury may also present as an intact or open/ruptured serum-filled blister. A stage three pressure injury may correspond to a full thickness tissue loss. At this stage, subcutaneous fat may be visible, but bone, tendon, or muscle are not exposed. Some sloughing of skin may be present. The depth of a stage three pressure injury may vary, depending on the anatomical location (e.g., nose, ear, hip, buttocks, etc.). A stage four pressure injury may correspond to a full thickness tissue loss with exposed (e.g., visible) bone, tendon, or muscle. In some examples, a pressure injury may be classified in a unique category (or stage) that may not directly correspond to one of the four possible stages discussed above. For example, a deep tissue injury (DTI) may be a unique form of a pressure injury. A DTI may correspond to a pressure-related injury to subcutaneous tissues under intact skin. Initially, these lesions may have the appearance of a deep bruise. These lesions may indicate the possibility of a subsequent development of a later stage pressure injury (e.g., stage three or four) even with proper service. In some cases, while a DTI may be difficult to detect, upon detection, it should be treated with more aggressive service to mitigate against rapid stage advancement. In some examples, a pressure injury may be classified as "unstageable." For example, ulcers covered with slough or eschar may be considered unstageable.

Continuing with the pressure injury stage prediction example, the prediction model may receive from the prediction system user data for a user, whereby the user data may include a plurality of data points. Each data point may be represented in any suitable form (e.g., text, image, video, audio). One or more features may be derived from the plurality of data points, which may be used by the prediction model to output a risk assessment. In this example, the risk assessment may include an indication of a particular stage of the user's pressure injury. It should be understood that, as described herein, a "stage" classification of a pressure injury may correspond to one of at least any of the stage classifications described above (e.g., stage one through four, DTI, and/or unstageable). For example, the risk assessment may include a probability score that corresponds to a likelihood that the particular pressure injury is a Stage 1 injury (e.g., 80%). In some examples, the prediction model may output a risk assessment that includes a probability score for each potential injury stage. Based on the risk assessment, a USP may determine an appropriate course of action. For example, the USP may determine that the user is a strong candidate to receive a wound consult. In another example, the risk assessment may also be used for updating documentation, to log the injury appropriately. Using the example above, assuming that the risk assessment was determined shortly after admission to the service unit (e.g., the hospital), the USP may log that the user likely has a Stage 1 community-acquired pressure injury (as opposed to a hospital-acquired pressure injury). In some examples, the stage prediction may be one of a plurality of indicators (e.g., probability scores) within the risk assessment. For example, the risk assessment may include a probability score indicating a likelihood of any pressure injury on the body as well as a probability score indicating a stage prediction, given the existence of the pressure injury. In some examples, the stage prediction may correspond to a level of severity of the injury. In some examples, the risk assessment may include a probability that a predicted stage will advance to the next stage (e.g. stage two to stage three) within a predetermined time interval (e.g., a median length of stay at the service unit for the condition under which the user was checked in).

In another example, a prediction model of the prediction system may utilize one or more images of a user's body to generate a risk assessment for a user. For example, a service device may capture images of a portion of a user's body. The prediction system may perform pre-processing steps to prepare the images to be input to the prediction model. For example, the system may standardize the images (e.g., to ensure the images have the same aspect ratio and size). The system may also determine features from the images (e.g., dividing the image into groups of pixels, where each group is a feature; determining color variations between pixel groups within the image, etc.). After performing the pre-processing, the features may be input into a trained image recognition model that is trained to automatically identify types of body conditions (e.g., moisture-associated dermatitis, skin tear, neuropathic skin ulcer (e.g., for a diabetic user), pressure injury, etc.). The image recognition model may, for example, be trained to distinguish moisture-associated skin damage (whereby the skin damage may be superficial and the edges are irregular or diffuse) from conditions (whereby the skin damage may have distinct edges). In some examples, the image recognition model may utilize a machine learning algorithm, such as a convolutional neural network that is trained based on receiving a number of images that is suitable for representing the population (e.g., images taken of users across multiple service facilities of the service organization). The image recognition model may then classify the injury as a particular type (e.g., a pressure injury at a particular body location) with a certain probability assigned. In some examples, the image recognition model may further be trained to predict (e.g., classify) a particular stage of the injury. In some examples, the image recognition model may then output these classifications as a risk assessment for presentation on a device. For example, the risk assessment may be used to determine if the user should receive a wound consult for the pressure injury. In some examples, the classifications output by the image recognition model may itself be used as an input feature to another prediction model, which may be trained to generate a risk assessment based on other inputs (e.g., the user's EMR, the clinician's notes, etc.).

In another example, a prediction system may receive user data for a user as input, and then output a holistic (e.g., overall) risk assessment for the user. The holistic risk assessment may correspond to a risk assessment that takes into account potential conditions on one or more locations on the user's body, and a predicted severity of each pressure injury at the respective location. In some examples, the holistic risk assessment may be generated based at least in part on outputs from a trained prediction model of the prediction system, which may be trained similar to as described above. For example, the prediction model may output a first risk assessment corresponding to a level of risk that a user has or will develop a first user injury at a first injury stage at a first body location. The prediction model may also output a second risk assessment corresponding to a level of risk that the user has or will develop a second user injury at a second injury stage at a second body location. The first and second risk assessments may, respectively, be weighted based at least in part on at least one of multiple possible factors (e.g., the injury stage, the body location of the injury, the size of the injury, the age of the user, etc.). This weighting of assessments may be based on data indicating that that different conditions may have different levels of severity (e.g., requiring varying levels of attention and/or service). For example, a stage three pressure injury wound on the buttocks may require more immediate attention than a stage one injury on the ears. The weighted risk assessments may be combined to determine a holistic risk assessment that indicates an overall severity level for the user. The holistic risk assessment may also be used to prioritize service for the user. For example, the user may be prioritized with respect to other users. Also, the USP may prioritize treating a first injury over a second injury on the same user (e.g., an injury that has advanced to a later stage and/or is in a location on the body that is at greater risk of advancing to a later stage).

In another example, a prediction model of the prediction system may utilize clinician notes of a clinician to generate a risk assessment for a user. For example, the prediction system may receive clinician notes from a clinician (e.g., via textual input, audio recording, etc.). Due to various demands on the clinician's time, the clinician may only input summary notes, which may not include a full diagnosis of possible conditions that the user may have. For example, a user who may have been admitted for a pelvic fracture may develop a pressure injury over the course of their service at the service unit, which may not be immediately visible (and/or may be a latent injury). The clinician may note, for example, that the user has difficulty with mobilization, and cannot turn on their side without assistance. Upon receiving the clinician's notes, the prediction system may input the notes into a trained machine learning model (e.g., a natural language processing (NLP)) model. The NLP model may have been trained based on a large number of data samples corresponding to clinician notes of users across the enterprise. As part of the training, the NLP may be trained to recognize indicators that correspond to one or more categories that are relevant to determining if a user may have a pressure injury. For example, the categories may correspond to features of a pressure injury prediction model (e.g., observed user mobility, observed pain reported by the user, service patterns observed during the course of service, etc.). In some examples, the NLP model may utilize word embeddings to derive context/meaning from the clinician's notes. The trained prediction may thus output, for a given clinician notes for a user, a plurality of indicators that each correspond to a relevant category. The prediction system may, in turn, input the plurality of indicators into a trained prediction model, similar to as described above. The trained prediction model may then output a risk assessment for the user that may be used by a USP to determine service for the user. It should be understood that the input received from the NLP model may be one of several inputs (e.g., along with blood lab results, etc.) to the prediction model.

In another example, a prediction system may determine a service bundle for a user based at least in part on determining a holistic risk assessment for the user. In some examples, the holistic risk assessment may be determined similar to as described above. For example, the prediction system may receive user data of a user, and input the user data into a trained prediction model of the prediction system. The prediction model may generate one or more risk assessments for the user (e.g., per pressure injury prediction), which may be combined to form a holistic risk assessment. The prediction system may utilize the holistic risk assessment to determine a customized service bundle for the user. In some examples, the prediction system may also use other information beyond the holistic risk assessment to determine the service bundle, including, but not limited to, a user's service history (e.g., known allergies and/or reactions to medication), other service the user is receiving for another (non-pressure injury related) injury and/or illness, etc. The customized service bundle may correspond to at least one of: (1) a type of service equipment recommended for the user, (2) a type of medication or service for the user, or (3) a frequency of service for the user. For example, the type of service equipment may include a service bed, a seat cushion, a foam, a heel protector, pressure-redistributing devices, etc. A type of medication or service for the user may include, for example, nonsteroidal anti-inflammatory drugs, topical pain medication, a particular bandage for the wound, etc. A frequency of service for the user may include, for example, a frequency for repositioning the user (e.g., if the user is otherwise immobilized), a frequency for the user receiving physical therapy, etc. It should be understood that the customized service bundle may account for the one or more conditions on the user's body, the particular stage and location of each injury, the age of the user, and other environmental factors. In some examples, the prediction system may maintain a record of user outcomes based on the service plans administered to the users. These records may be used to train the prediction system to recommend better bundle service plans. For example, the prediction system may identify a particular pattern (e.g., increased number of conditions) from users that were treated with a similar service equipment (e.g., a type of service mask), and, based on this observed pattern, recommend that users at a higher risk for conditions should not be prescribed this type of service mask.

In another example, a prediction system may determine a procurement system for service equipment based at least in part on determining risk assessments for users of the service system. For example, the prediction system may receive user data from a plurality of service facilities of a service association affiliated with the prediction system (e.g., via a service management system). A prediction model of the prediction system may output risk assessments for each user across the service organization (e.g., segmented per facility, per division, per department of a particular facility, etc.). These risk assessments may be determined on a suitable cadence, for example, once a week or once a month. Then, based on these risk assessments over time, the prediction system may generate a report. In some examples, the report may indicate predicted demands for pressure injury-related service equipment based on historical patterns over time. For example, in the case of a per-department segmentation, the prediction system may determine that the Intensive service Unit (ICU) trauma department at a particular service facility has a relatively higher number of users that are at high risk of a pressure injury, and which may be immobilized. In some cases, the system may further determine that the number of users with conditions in the ICU trauma department increases during certain seasons (e.g., during summer time or winter time). The system may recommend, based at least in part on this report, that a certain number of service equipment be procured for the ICU trauma department at the particular facility. For example, the system may determine to procure service bed units that are designed to mitigate against risk of conditions advancing. It should be understood that, in some cases, procuring service units may include purchasing or renting service units. In other cases, it may involve transferring service units between facilities in the service organization in order to meet anticipated load in another facility. In this way, the procurement process for service equipment used to prevent conditions may be standardized and made more efficient.

The present disclosure provides several technical advantages over existing solutions that improve the functioning of the computer system in which a prediction system is implemented. For example, conventional techniques include utilizing a significant amount of computing and/or human resources to detect and address conditions. For example, a USP may first detect a potential pressure injury. The USP may then exchange a number of electronic messages with another USP (e.g., from a wound consult team) to determine a severity of the wound, and whether specialized service for the user is desired. A substantial number of messages between USPs may be exchanged for a large number of users, since the triage USP may not be able to immediately identify (e.g., triage) the level of risk, and therefore may need to involve other USPs. However, examples of the present disclosure may reduce the total number of message required per user. For example, the prediction system may automatically classify users as low risk, medium risk, or high risk. Based on this assessment, the prediction system may recommend a much smaller set of users that require service from a wound consult team, which may in turn decrease the number of message exchanges. By reducing the total number of messages required per user, multiplied over a large number of users in a service system, this may improve network efficiency (e.g., increasing available bandwidth) and increase computing resources available to the computer system. This may also lead to improved memory utilization because the number of messages required for processing and storage is reduced. Additionally, because the systems and predictive models are trained using the largest and most relevant datasets available (i.e., those maintained in the world's largest clinical data warehouse), the predictions made using the described system are more precise and more accurate than those made by prior art systems trained using smaller datasets. For example, these datasets may be drawn from user data including a large corpus of images (of conditions on a body), clinician notes, blood samples, etc. Additionally, because of the higher quality of the prediction models, fewer computing resources are required to make the predictions as would be required using conventional techniques.

Figure 11:
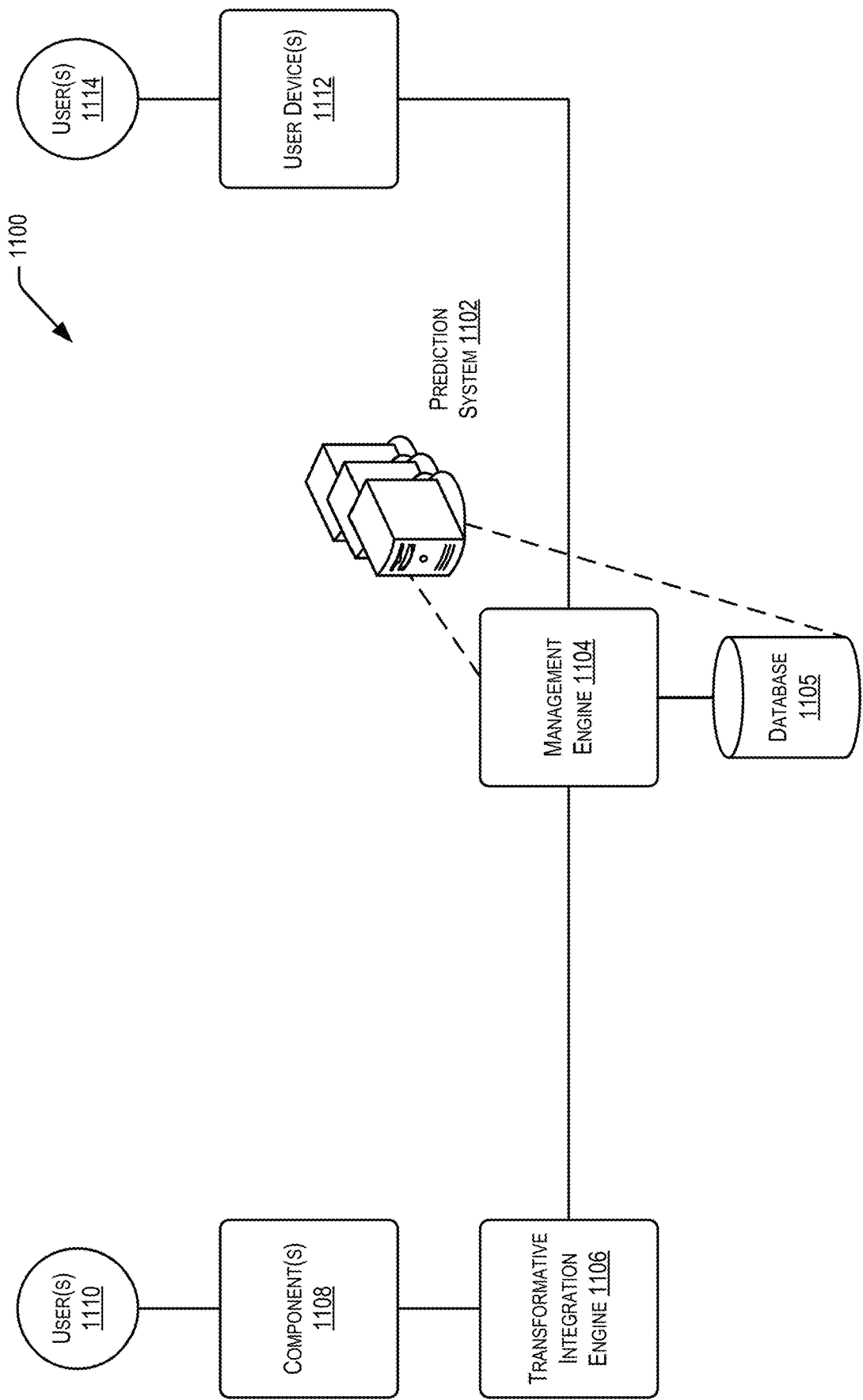
FIG. 11 is an example architecture illustrating a system in which techniques relating to providing a risk assessment that a user has or will develop a condition may be implemented, according to at least one example.

Turning now to FIG. 11, a prediction architecture 1100 is shown, in accordance with at least one example. The prediction architecture 1100 may be implemented using elements of the systems, networks, and models of FIGS. 1-10. For example, the prediction architecture 1100 may include similar elements as service provider prediction system 900 of FIG. 9. For example, the prediction architecture may include a prediction system 1102, which includes a management engine 1104 (e.g., prediction model management engine 902) and a database 1105 (e.g., included within data store 915). The prediction architecture 1100 may further include a transformative integration engine 1106 (e.g., similar to transformative integration engine 202 of FIG. 2). The transformative integration engine 1106 may be configured to receive and process data from one or more generation components 1108 (e.g., similar to generation components 204 of FIG. 2), which may in turn receive input from one or more generation users 1110 (e.g., user service providers (USPs), users, and/or other service professionals) to generate service-related data. The prediction architecture 1100 may further include one or more user devices 1112 (e.g., similar to user device 228), which may be used to interact with users 1114 (e.g., USPs and/or other service professionals).

In some examples, the prediction system 1102 may be configured to receive data from the transformative integration engine 1106 and utilize the data to generate one or more predictions (e.g., risk assessments) that may be displayed on a user device 1112 of a user 1114. The transformative integration engine 1106, described in detail herein, can process and store data used by a prediction system 1102 to implement the techniques described herein. For example, the management engine 1104 of the prediction system 1102 may receive user data from the transformative integration engine 1106 and use the user data to train one or more prediction models. The user data may include user service records, interaction data (e.g., between the user and a USP), feedback data, outcome data, and the like. The user data may be representative of users within a population. At a later time, the management engine 1104 may receive current user data (e.g., for a currently admitted user) which is input into one of the trained prediction models. The trained prediction model may then output a prediction (e.g., a risk assessment of whether a user may have a pressure injury) to user device 1112 for use by a USP in determining a service plan for the user (e.g., whether the user should receive a wound consult from a USP member of a wound consult team).

The database 1105 is accessible by the management engine 1104, and may be similar to (or connected to) data store 915 of FIG. 9 and/or data store 226 of FIG. 2. The database 1105 may access user data from a transformative integration engine 1106 and use such data to generate risk assessments for a USP. For example, the user data may include training data and testing data (e.g., to test the prediction models). The database 1105 can be distributed or otherwise made available to multiple users. In some examples, the database 1105 may be centralized. In other examples, the database 1105 may be decentralized (e.g., a database per division or per service facility). In some examples, the database 1105 may store multiple prediction models. It should be understood that, although in the examples described herein, multiple types of prediction models may be described, the functions performed by the one or more prediction models may also be performed within a single prediction model or any suitable combination of models, as described in reference to FIGS. 9 and 10. The prediction models, as described herein, can be initialized using data mined from the data store of the transformative integration engine 1106.

The prediction system 1102 may be affiliated with a service management system of a service organization (e.g., enterprise), whereby the service management system may also be implemented using similar elements of the systems, networks, and models of FIGS. 1-10. For example, the service management system may be a centralized system for performing techniques described herein. The centralized system may aggregate user data (e.g., via the transformative integration engine 1106) from a plurality of affiliated service facilities of the service organization into a data store (e.g., data store 226) for further processing by the prediction system 1102.

Examples described herein provide different systems and methods for supporting a USP (e.g., a nurse, physician, administrator) in the process of coordinating user service. The systems and methods provided are suitable to support a USP in a variety of environments and contexts. For example, some environments may involve coordinating user service across an entire enterprise or a division of the enterprise that contains multiple service facilities. Another environment involves coordinating service among users in a single service facility, and/or users within a particular department within the single service facility. In another example of a particular context, the system may help the USP coordinate service for a user at the time of admission to a service facility, while the user is receiving service during their stay, or post-discharge. These various environments and contexts will be discussed herein below.

Figure 12:
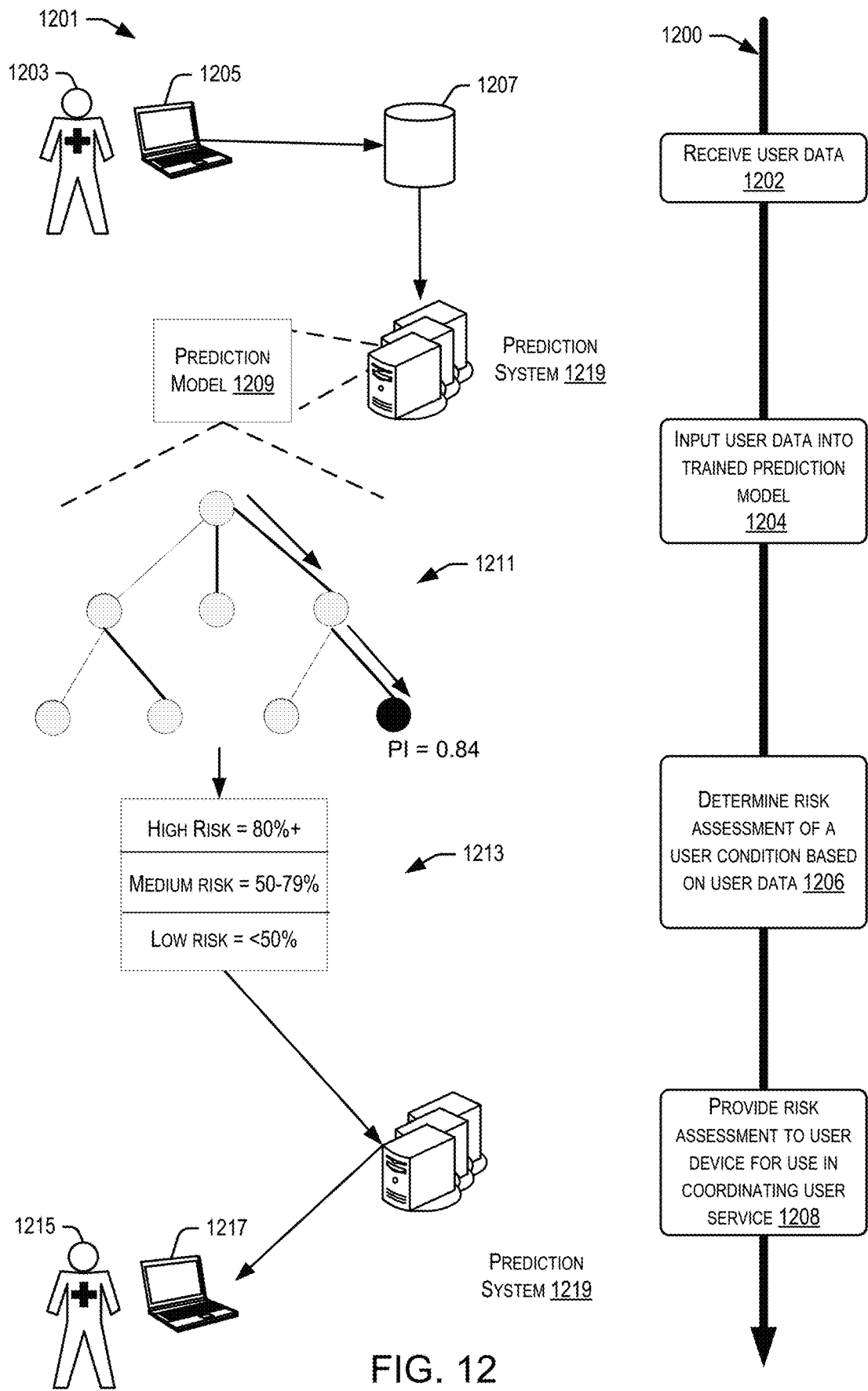
FIG. 12 is an example diagram illustrating a process for providing a risk assessment that a user has or will develop a condition, according to at least one example.

FIG. 12 illustrates a simplified block diagram 1201 depicting an example process 1200, in accordance with at least one example. The process 1200 is an example process for generating a risk assessment of a pressure injury for a user using a trained prediction model. The diagram 1201 depicts example states that correspond to the blocks of the process 1200. The diagram 1201 includes devices 1205 and 1217, a data store 1207 (e.g., which may be similar to data store 226 of the transformative integration engine 202), and prediction system 1219 (e.g., which may be similar to prediction system 1102 of FIG. 11), that perform at least a portion of the process 1200.

The process 1200 begins at block 1202 whereby a prediction system receives, from a device, user data for a particular user. For example, device 1205 may be operated by a USP of a service facility and may receive input related to the particular user's service/condition. For example, the device 1205 may correspond to a generation component (e.g., generation component 906 of FIG. 9), such as a blood chemistry analyzer, a laptop, a service imaging device, etc. Upon receiving input, the device 1205 may transmit the user data for the particular user over a network to the prediction system 1219 (and/or an affiliated service management system) for storage in data store 1207 of the service management system. The user data may be incorporated into a new or existing user service record of the user. The service facility may be one of several service facilities maintained by a service organization. The service organization may maintain the service management system that is configured to receive data (e.g., user service records, lab test results, etc.) from each of the service facilities (e.g., into the centralized data store 1207 of the service management system). It should be understood that, although in this example, a user data for a single user is described, in other examples, user data for multiple users may be received (e.g., for an entire service facility, department within a facility (e.g., Emergency Department), division, or enterprise). The user data may be received according to any suitable cadence (e.g., whenever a user's record is updated, or on a predetermined schedule).

At block 1204, the prediction system 1219 may input the received user data into a trained prediction model 1209 of the prediction system 1219. The trained prediction model 1209 may be trained to output a risk assessment corresponding to a level of risk that the particular user has or will develop a pressure injury. As described above, in some examples, prediction system 1219 may be affiliated with the service management system. In some examples, the prediction system 1219 may be a component of the service management system. In some examples, the prediction system 1219 may retrieve the user data from the data store 1207 of the service management system for input into the trained prediction model 1209. The trained prediction model 1209 may be trained based at least in part on features derived from user training data from multiple users previously collected by the service management system (across the different service facilities of the service organization). Each training data sample of the training data may include multiple data points, as described below in relation to Table 1 and FIG. 13. The prediction model may be trained according to one or more machine learning algorithms, as described in reference to FIG. 10 (e.g., blocks 1002-1006). For example, as depicted in FIG. 12, the prediction model may utilize one or more decision trees 1211 (e.g., a boosting decision tree model). The training data may be used to configure nodes and interconnections between nodes of each decision tree 1211, in order to maximize information gain, balance variance and bias, and improve specificity and sensitivity values. As discussed herein, the prediction model may utilize an ensemble of models to generate a risk assessment. For example, a neural network model may be trained to recognize pressure injuries in images taken of a user. The output of the neural network model (e.g., a probability and/or classification of the predicted type of injury) may be a feature (of a plurality of features) that is input to the trained prediction model 1209. The received user data for the particular user may include similar data points as the training data samples that were used to train the prediction model.

At block 1206, the prediction model 1209 of the prediction system 1219 may determine a risk assessment of a pressure injury for the particular user based at least in part on the received user data. For example, continuing with the boosted decision tree model 1211 example, the plurality of data points of the user data may respectively correspond to one of a plurality of categories, including, for example, the user's age, BMI, blood quality, heart quality, and/or body healing indicators (see FIG. 13). The data points may further be mapped to features by which the prediction model 1209 was previously trained. Based on values for each of these features, the boosted decision tree model 1211 may output a probability of (pressure) injury ("PI") at a leaf node (e.g., 84%). Although, in the example of FIG. 12, only one decision tree is depicted, it should be understood that an ensemble of trees may be used to determine the PI, as discussed in reference to FIG. 10. In some examples, a level of risk of a pressure injury may further be determined based at least in part on one or more predetermined threshold values (or ranges) 1213. For example, as depicted in FIG. 12, the predetermined threshold values may correspond to a "High Risk (of pressure injury)" (e.g., 80%), "Medium Risk" (e.g., 50-79%), or "Low Risk" (e.g. 50%). In this example, a PI of 84% would correspond to a high risk of injury. As discussed in various examples herein, the risk assessment may reflect one or more aspects of the user's condition, beyond a level of risk of a particular pressure injury. For example, the risk assessment may indicate levels of risk for multiple pressure injuries on the user's body. The risk assessment may further indicate a predicted severity level for a pressure injury, which may be associated with a stage of the pressure injury and/or a location on the body of the particular pressure injury.

At block 1208, the prediction system 1219 may provide the determined risk assessment to a user device (e.g., of a USP) for use in coordinating user service. For example, the prediction system 1219 may provide the risk assessment for presentation at the user device 1217. In some examples, the risk assessment may be transmitted and/or stored by the service management system before being provided for presentation. In some examples, the prediction system 1219 may be configured to compute risk assessments for one or more users on a predetermined schedule (e.g., several times a day). In some examples, the risk assessments may be provided by the prediction system 1219 to the user device 1217 for presentation immediately upon being generated. In other examples, the prediction system 1219 may provide a daily report including all the runs for that day. In some examples the one or more risk assessments may be presented on a dashboard of the user device 1217, as discussed herein.

Figure 13:
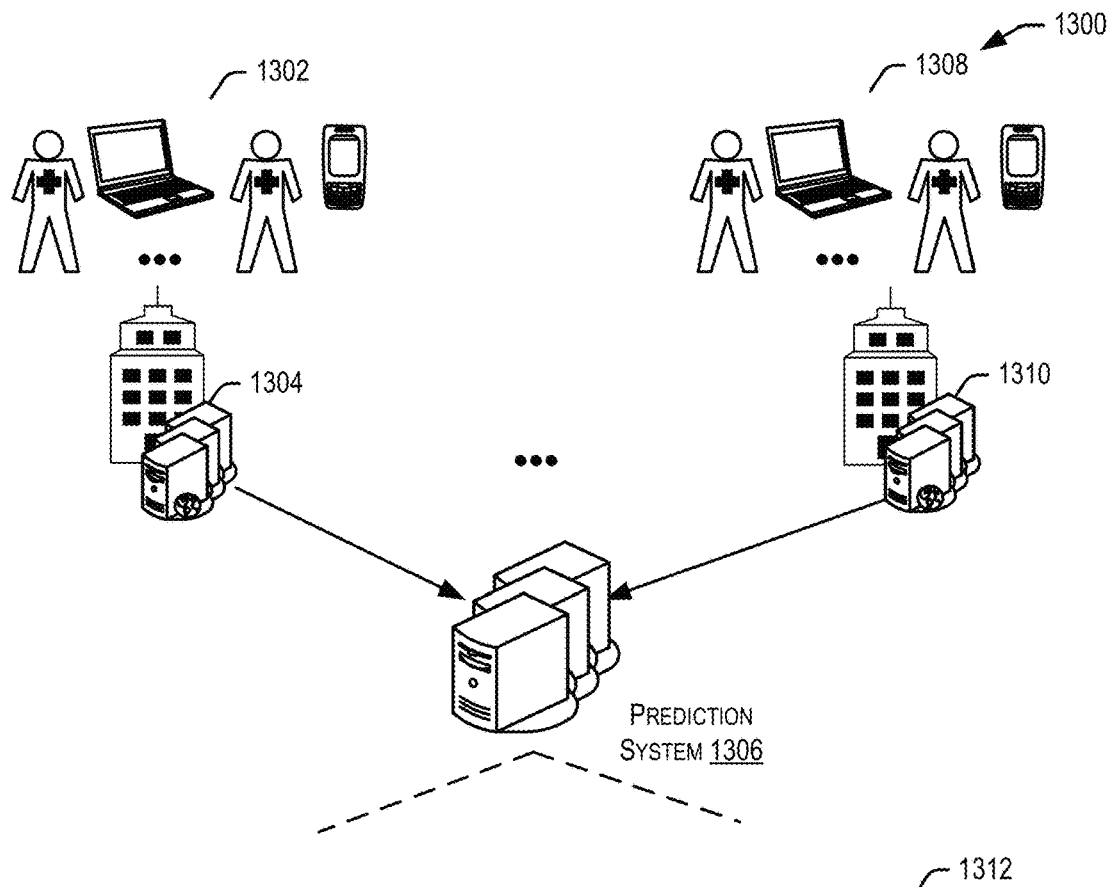
FIG. 13 is an example flowchart illustrating a process for training a prediction model of a prediction system, according to at least one example.

FIG. 13 illustrates a simplified block diagram 1300 depicting a technique for training a prediction model of a prediction system, in accordance with at least one example. The diagram 1300 depicts a plurality of service facilities (e.g., represented by 1304 and 1310). Each service facility may be associated with (e.g., employ) one or more USPs (e.g., 1302 and 1308). Each USP may be responsible for service for one or more users. A device may receive input from a USP and generate user data that is transmitted to the prediction system 1306 (e.g., which may be similar to prediction system 1102 or 1219). Each service facility may be affiliated with a service organization that maintains a service management system. The service management system may be responsible for receiving data from a variety of facilities, systems, etc., and standardizing the data (e.g., via a transformative integration engine 904). Accordingly, the user data received by the prediction system 1306 may be representative of a large number of users (e.g., over 300,000 users of a service organization). This user data may be used to define one or more sets of training data, as described in reference to FIGS. 9 and 10 (e.g., the data preparation engine 914 of FIG. 9). The one or more sets of training data may be stored in a data store (e.g., data store 915) of the prediction system 1306. In some examples, only a relatively small percentage of the users sampled (e.g., 0.1%) may actually have a pressure injury. By utilizing user data over a large number of users of the service organization and training the prediction model as described herein, examples of the trained prediction model described herein may increase the sensitivity (also known as "recall" or "true positive rate") and the specificity (also known as the "true negative rate") of the prediction model beyond rates achieved through conventional methods.

As described earlier, training data samples generated by the prediction system 1306 may each include a plurality of data points (e.g., over 40 different data points (or variables)). Each data point may correspond to one or more of a plurality of possible categories, including, for example, age, BMI, blood quality, heart quality, body healing indicators, user admission/service data, etc. Table 1 below describes examples of data points that may be collected by the prediction system 1306. It should be understood that some of the data point examples of Table 1 may at times fit more than one category, and are intended to be representative, not an exhaustive list. For example, the "White Blood Cell" (WBC) may be applicable to both the heart quality and body healing indicators categories. Also, in some examples, a minimum ("min") and/or maximum ("max") value may be associated with each data point. For example, the "Glucose" data point may be associated with a "min glucose" value and a "max glucose" value, which may respectively indicate a minimum and maximum level of glucose in the blood over an observed period of time.

TABLE 1

Example Patient Data Points (which may be used to train a prediction model or as input to a trained model)

| Example Patient Data Categories | Examples of Patient Data Points per Category |
|---|---|
| Blood Quality | Anion Gap |
| | Sodium |
| | Potassium |
| | Glucose |
| | Bilirubin |
| | Carbon Dioxide |
| | Creatinine |
| | Hemoglobin |
| | Hematocrit |
| | Pulse Oximetry |
| Body Healing (Health) Indicators | White blood cell (WBC) |
| | Alanine aminotransferase (ALT) |
| | Ensophil |
| | Albumin |
| | C-reactive protein (CRP) |
| | Vasopressin Medication |
| | Diabetes Medication |
| | Body Temperature |
| | Ambulation |
| | Incontinence |
| | Sepsis |
| | Quadriplegia/Paraplegia |
| | Taking steroid medication |
| | Number of days on ventilator |
| | Duration of surgical procedure |
| | Total Parenteral Nutrition (TPN) |
| | Amputation |
| Heart Quality | Troponin |
| | Lactate |
| | Blood pressure |
| | Pulse |
| | Brain natriuretic peptide (BNP) |
| | Chloride |
| | Blood Thinner Medication |
| | Blood Urea Nitrogen (BUN) |
| Patient Age | Patient Age |
| Patient Body Mass Index (BMI) | Patient BMI |
| Patient Sex | Patient Sex |
| Patient Admission/ Treatment Data | Admitting Unit |
| | Admitting Practitioner |
| | Admit Month |

In some examples, the prediction system 1306 may utilize the plurality of data points (over the corpus of training samples) to train the prediction model. The plurality of data points may be used to determine (e.g., derive) features of the prediction model. In some examples, there may be a one-to-one correspondence between a data point and a feature. In some examples, one or more data points may be analyzed (e.g., transformed, combined, separated, etc.) to form a feature. For example, a data point that corresponds to an image of the user's body may be transformed into one or more features (e.g., pixel-based segments of the image), which are then used to train the prediction model. As a product of training the prediction model, and as described in reference to FIG. 10, the prediction system 1306 may be able to determine a relative importance of features among the set of features used to train the prediction model. For example, consider an example where the prediction model utilizes a boosted decision tree. In this example, the boosted decision tree may be trained based at least in part on features that respectively correspond to the data points described in Table 1 above. The relative importance of the features may be represented in a ranking table, for example, as depicted in ranking table 1312 of FIG. 13. In ranking table 1312, a subset of features/data points of Table 1 are depicted, which, in this example, are features that were determined to be predictive when generating a risk assessment of a pressure injury. In this example, "age" is ranked as most important feature in determining a level of risk that the user has a pressure injury. The "min creatinine" feature is ranked as being 97.9% as important as age. The "min albumin" is ranked as being 91.8% as important as age. Thus, the features of ranking table 1312 are ranked in descending order of importance, relative to the most important predicting feature, and thereby, relative to each other. It should be understood that other ranking orders (and/or values) may be suitable for performing examples of the present disclosure.

Figure 14:
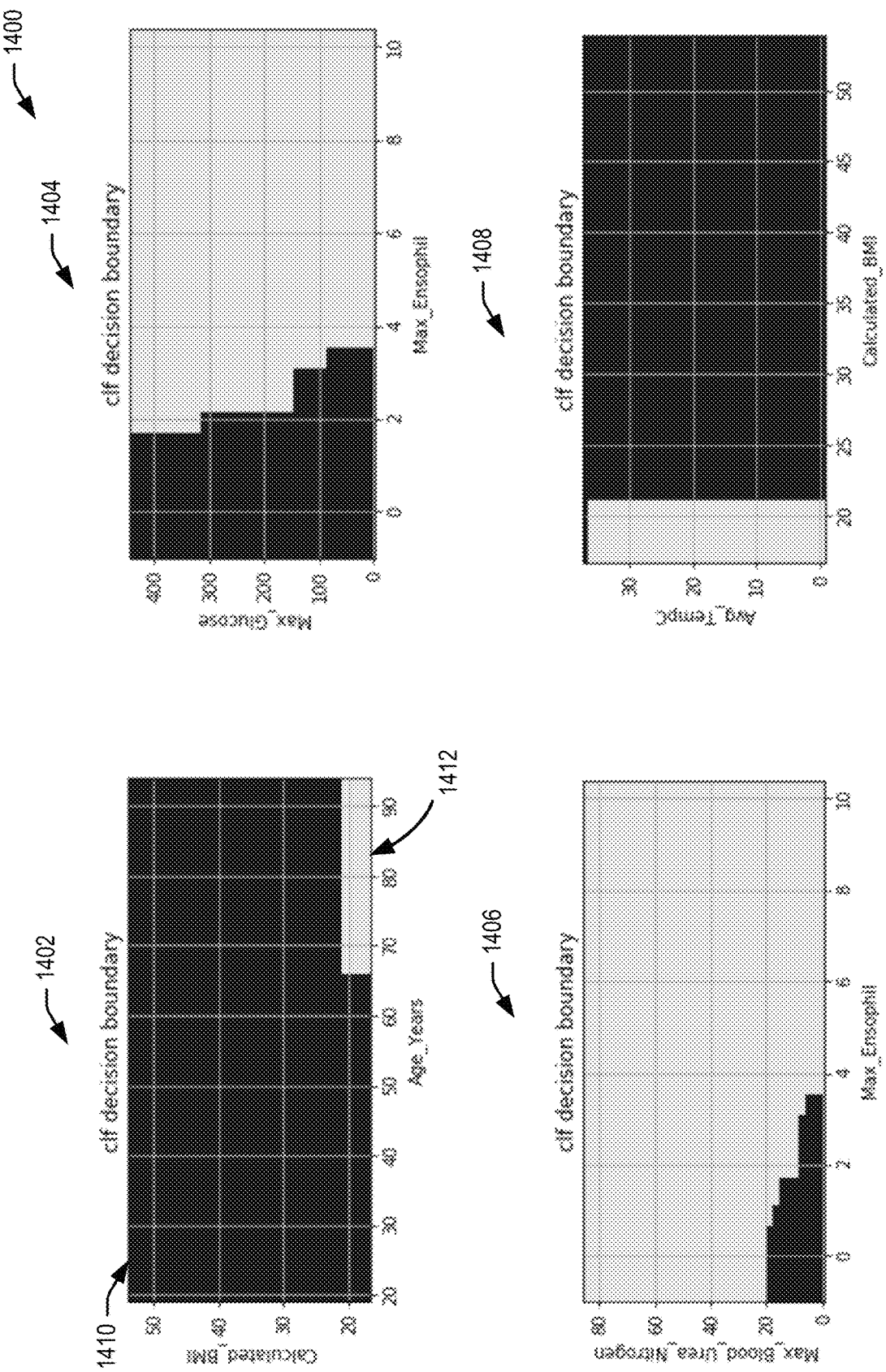
FIG. 14 is an example diagram illustrating techniques for training a prediction model of a prediction system, according to at least one example.
Figure 15:
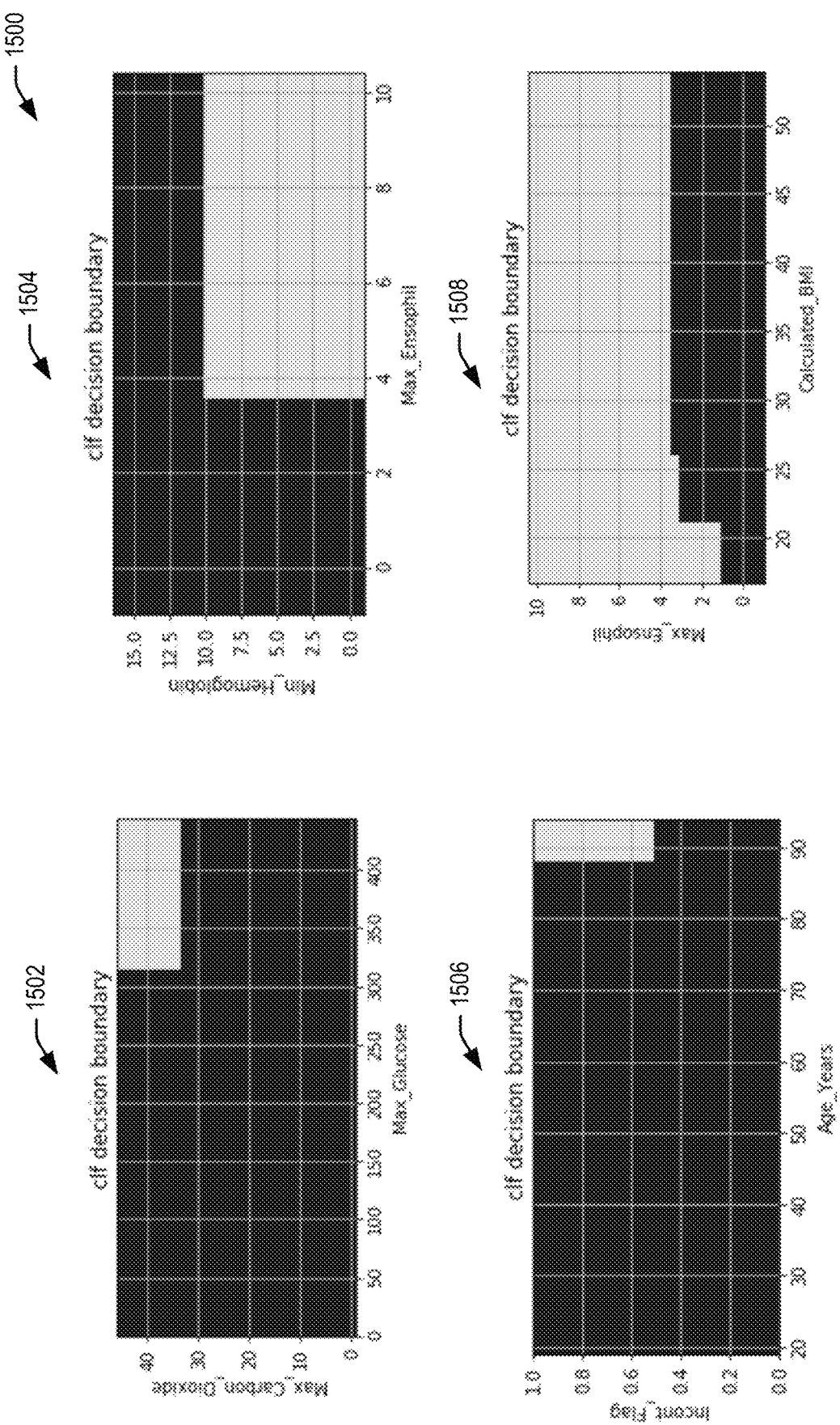
FIG. 15 is an example diagram illustrating techniques for training a prediction model of a prediction system, according to at least one example.
Figure 16:
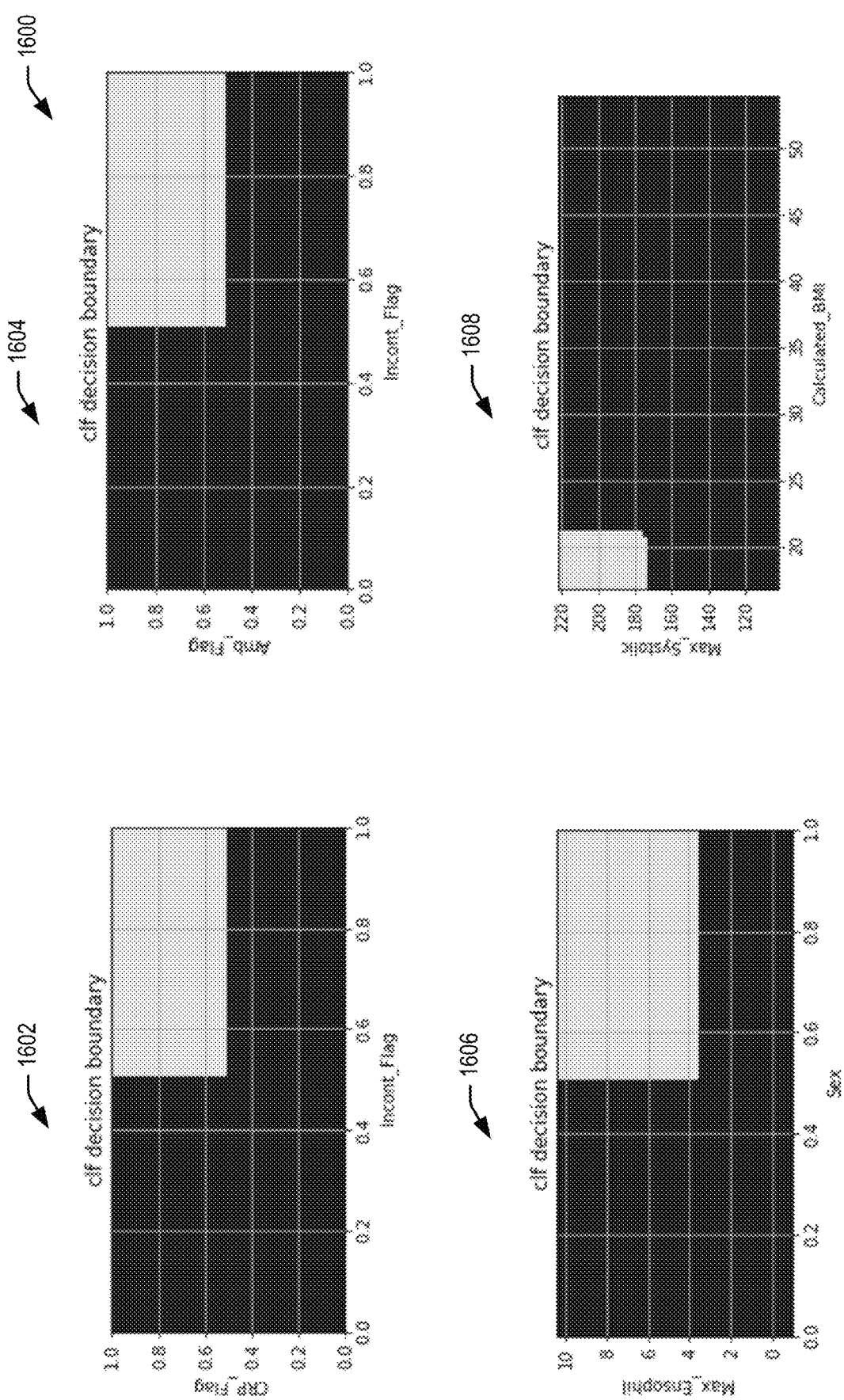
FIG. 16 is an example diagram illustrating techniques for training a prediction model of a prediction system, according to at least one example.

FIGS. 14, 15, and 16 illustrate simplified block diagrams (1300, 1400, and 1500) depicting techniques for training a prediction model of a prediction system, in accordance with at least one example. As a product of training the prediction model, and as described in reference to FIG. 10, the prediction system may also be able to determine one or more classifier decision boundaries (CDBs). For example, continuing with the example where the prediction model utilizes a boosted decision tree, the prediction system may be able to determine classifier decision boundaries based at least in part on the training process used to determine splits for each node in the ensemble of decision trees. As described herein, a classifier decision boundary may partition an underlying partition vector space into two sets (e.g., classes). In some examples, the vector space may be depicted on a scatter plot, whereby every point depicts a data point of a training data sample (among a corpus of training data samples plotted), and the axes depict features. Each of FIGS. 14, 15, and 16 depict four classifier decision boundary diagrams, whereby each diagram demarcates a decision boundary based on two features among the set of features used to train the prediction model. In some examples, each of the diagrams may be generated based at least in part on a scatter plot of data points (not shown). It should be understood that the twelve diagrams depicted in FIGS. 14, 15, and 16 are intended to be exemplary CDBs that may be determined based on the prediction model training process, not an exhaustive list.

As an example, diagram 1402 depicts a CDB between the two features of age ("age_years") and BMI ("calculated_BMI"). The lighter shade region 1412 of the diagram 1402 depicts a range of values for data points of a sample under which a user would be classified as having a pressure injury. The darker shade region 1410 of the diagram 1402 depicts a range of values for data points of a sample under which a user would be classified as not having a pressure injury. In diagram 1402, the CDB indicates that a user whose age is greater than the mid-60's and whose BMI is less than the low-20's would be classified as likely having a pressure injury. Similarly, diagram 1404 depicts a CDB between the two features of ensophil (i.e., "max_ensophil") and glucose (i.e., "max_glucose"). In this example, a user with a higher "max ensophil" value (e.g., which may be used to detect a number of white blood cells that fight disease) may be more likely to be classified as having a pressure injury with respect to a range of "max_glucose" values.

In some examples, a classification based on a CDB may correspond to a single input among multiple inputs (e.g., from multiple CDBs). Thus, for example, consider a user who is 75 years old and has a BMI of 18. The user also has a "max_ensophil" level of 2 and a "max_glucose" level of 100. In this example, the CDB of diagram 1402 may indicate that the user likely has a pressure injury, while the CDB of diagram 1404 may indicate that the user likely does not have a pressure injury. The outputs from each of these diagrams may be combined, for example, based in part on the relative rankings (e.g., weights) for the different features, as described in reference to FIG. 13. The final output of the prediction model may thereby incorporate multiple decision boundaries into a single classification (e.g., a probability score between 0-1). It should be understood that, among the potential data points considered when training a prediction model (e.g., see Table 1), the relationships between particular data points, for example as depicted in each of the diagrams, may correspond to a higher predictive value within the predictive model.

Continuing with the other example diagrams of FIGS. 14, 15, and 16, diagram 1406 depicts a CDB between the two features of ensophil (i.e., "max_ensophil") and BUN (i.e., "max_blood_urea_nitrogen"). In this example, a user with a lower "max ensophil" value and a lower max_BUN value may be less likely to be classified as having a pressure injury. Diagram 1408 depicts a CDB between the two features of BMI ("calculated_BMI") and body temperature ("avg_tempC"). In this example, a user with a low BMI may be more likely to be classified as having a pressure injury with respect to a range of body temperature values.

Turning to FIG. 15, diagram 1502 depicts a CDB between the two features of glucose (i.e., "max_glucose") and carbon dioxide (i.e., "max_carbon_dioxide"). In this example, a user with a higher "max glucose" value and a higher "max_carbon_dioxide" value may be more likely to be classified as having a pressure injury. Diagram 1504 depicts a CDB between the two features of ensophil (i.e., "max_ensophil") and hemoglobin (i.e., "min_hemoglobin"). In this example, a user with a higher "max_ensophil" value and a lower "min_hemoglobin" value may be more likely to be classified as having a pressure injury. Diagram 1506 depicts a CDB between the two features of age (i.e., "age_years") and incontinence (i.e., "incont_flag"). In this example, a user with a higher age and that tests positive for incontinence may be more likely to be classified as having a pressure injury. Diagram 1508 depicts a CDB between the two features of ensophil (i.e., "max_ensophil") and BMI ("calculated_BMI"). In this example, a user with a higher "max_ensophil" value may be more likely to be classified as having a pressure injury for a range of BMI values, with a slightly higher chance of having a pressure injury at lower BMI values.

Turning to FIG. 16, diagram 1602 depicts a CDB between the two features of incontinence (i.e., "incont_flag") and CRP (i.e., "CRP_flag"). In this example, a user that tests positive for C-Reactive protein (CRP) and tests positive for incontinence may be more likely to be classified as having a pressure injury. Diagram 1604 depicts a CDB between the two features of incontinence (i.e., "incont_flag") and ambulation (i.e., "amb_flag"). In this example, a user that tests positive for incontinence and that tests positive for ambulation issues (e.g., not being ambulatory) may be more likely to be classified as having a pressure injury. Diagram 1606 depicts a CDB between the two features of sex ("sex") and ensophil (i.e., "max_ensophil"). In this example, a user that has a higher "max_ensophil" value and that is a woman (i.e., represented with a value of 1.0) may be more likely to be classified as having a pressure injury. Diagram 1608 depicts a CDB between the two features of BMI (i.e., "calculated_BMI") and blood pressure (i.e., "max_systolic"). In this example, a user that has a lower BMI and a higher systolic blood pressure may be more likely to be classified as having a pressure injury.

Figure 17:
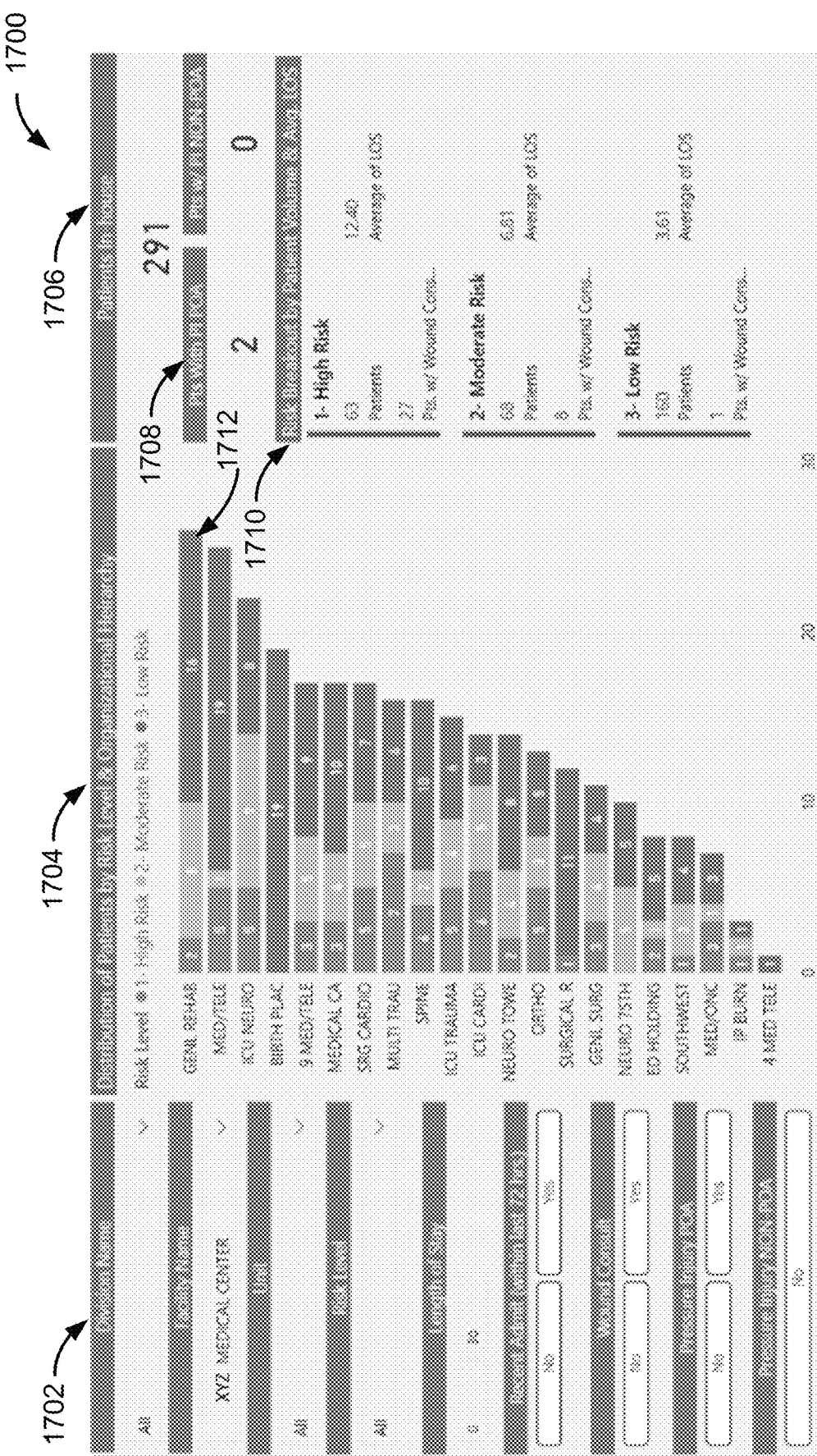
FIG. 17 is an example diagram illustrating a graphical user interface (GUI) for providing a risk assessment that a user has or will develop a condition, according to at least one example.

FIG. 17 illustrates a graphical user interface (GUI) 1700 of a display of a user device, according to at least one example. In some examples, the user device may be similar to user device 1217 of FIG. 12 and/or user device 1112 of FIG. 11 (e.g., a mobile device). In some examples, the GUI 1700 may correspond to a dashboard presentation of an application executing on the user device. In an example, the application may be provided for a USP of the enterprise. The application may allow the USP to see distributions of users according to risk level based on one or more applied filters. In some examples, the applied filters may enable a USP to view one or more levels of the organizational hierarchy within the enterprise. The GUI 1700 of FIG. 17 depicts a facility level view (e.g., "XYZ Medical Center") within an organizational hierarchy that depicts a distribution of users with varying levels of risk within different units (e.g. departments) of the facility. This may enable the USP to better prioritize which users/units require more attention. It should be understood that, as described in reference to FIGS. 17 and 18, a prediction system (e.g., prediction system 1219 of FIG. 12) may be utilized to generate risk assessments that are then used to populate data within the respective GUIs. For example, risk assessments generated by prediction model 1209 may be used to populate the facility level view of GUI 1700, grouping users according to risk levels per facility unit, as described below. In another example, the risk assessments may be used to populate risk levels (e.g., probability scores) for individual users, as described below in reference to GUI 1800 of FIG. 18.

Turning to GUI 1700 in further detail, column 1702 may present a USP with options for filtering. Based on the one or more filters selected from column 1702, the GUI 1700 may display a customized organizational view 1704. The GUI 1700 may also display additional statistics (e.g., elements 1706, 1708, 1710) based on the filters selected from column 1702.

In some examples, and as depicted with regards to column 1702, the GUI 1700 may allow a USP to filter by Division Name, Facility Name, Unit, Risk Level, Length of Stay, users that are recent admits (e.g., within the last 72 hours), users that have (or have not) received a wound consult, users for which a pressure injury was determined to be present on admission (POA), and/or users for which a pressure injury was determined to not be POA. In this example, as described above, the "XYZ Medical Center" facility is selected. Also, the length of stay is set to be within 0-30 days, and users with pressure injuries that were determined to not be POA are included.

Within the organizational view 1704, the distribution of users according to risk level is displayed. In this example, the distribution is displayed according to units within the particular facility (e.g., General Rehab, etc.). A bar graph may indicate, for a given unit, the breakdown of users who are of high risk, moderate risk, or low risk. Using the "General Rehab" unit as an example, bar graph 1712 depicts 2 users at high risk, 8 users at moderate risk, and 16 users at low risk within the unit. Note that in the example of view 1704, the "Birth Place" unit has 19 users who are all at low risk. Contrast that with the "Multi Trauma" unit, which has the highest number of high risk users (e.g., 7 users) for pressure injuries relative to other units.

Finally, several statistics may be displayed for presentation. For example, GUI 1700 depicts the total number users in-house 1706 (e.g., 291), which may be used as a contextual reference when analyzing other statistics. Also, the total number of users with a pressure injury (PI) that was POA 1708 may be displayed (e.g., 2). A risk breakout view 1710 that groups users according to high risk, moderate risk, and low risk, across the entire facility, may also be displayed. Note that these are representative examples, and any suitable statistics may be displayed for presentation.

In some examples, as described herein, the presentation of GUI 1700 may be used by a USP to coordinate service for users that may have a pressure injury. For example, a USP may utilize this presentation to determine a number of service equipment (e.g., specialty service beds) that should be procured for each unit of a service facility. In some cases, this procurement may involve determining that one unit (e.g., the "Birth Place" unit) may loan a service bed to the "Multi Trauma" unit, based in part on the higher number of users at high risk for a pressure injury in the "Multi Trauma" unit. In other examples, the USP may determine how to allocate human resources to meet demand. For example, the presentation may be used by a USP to determine how to allocate members of the wound consult team to different units. In some examples, the prediction system may utilize the outputs of the prediction model to automatically recommend/coordinate service equipment and/or human resource allocation within the service facility.

Figure 18:
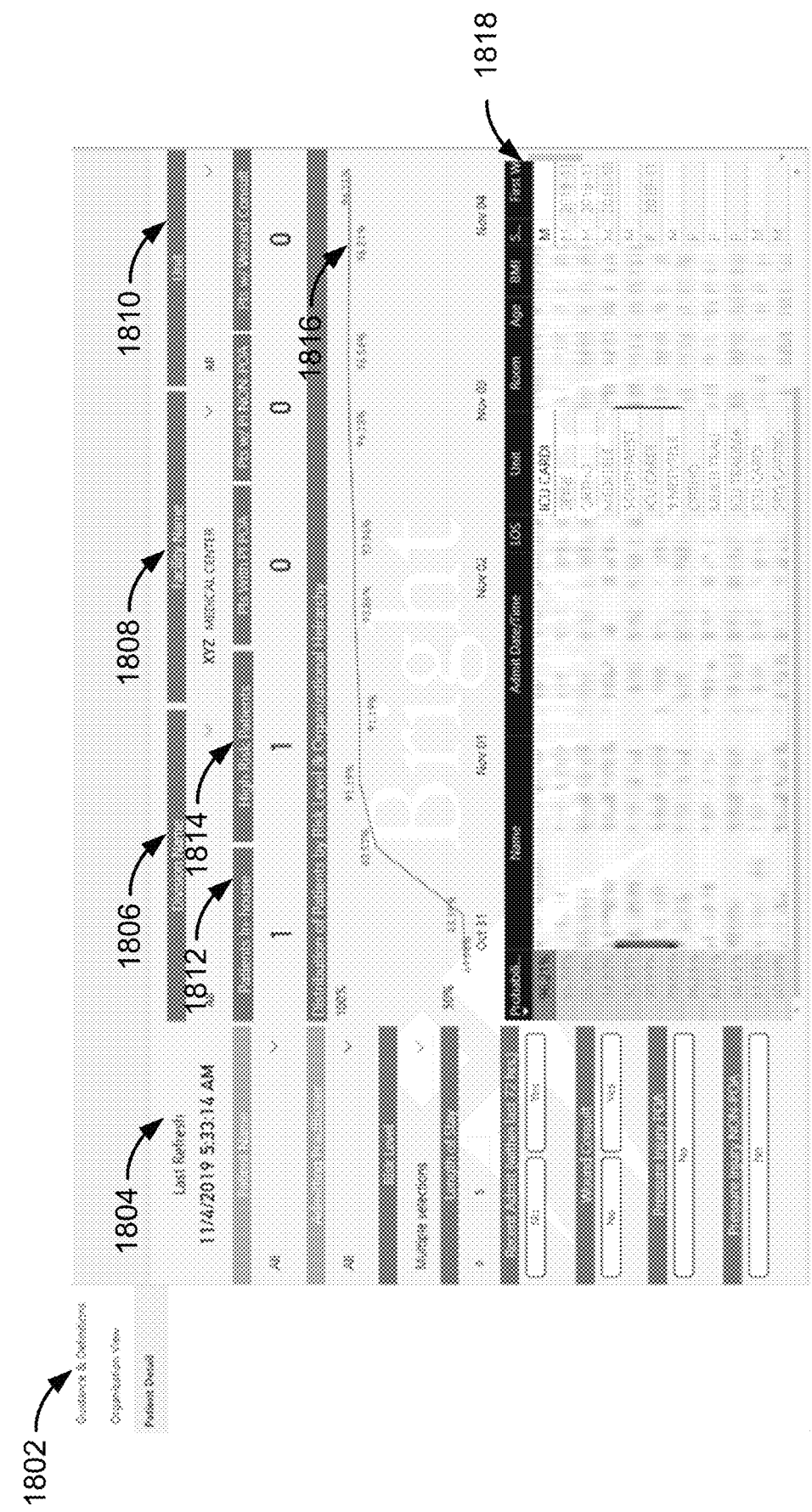
FIG. 18 is an example diagram illustrating a GUI for providing a risk assessment that a user has or will develop a condition, according to at least one example.

FIG. 18 illustrates another graphical user interface (GUI) 1800 of a display of a user device. Similar to FIG. 17, the user device may be similar to user device 1217 of FIG. 12 and/or user device 1112 of FIG. 11 (e.g., a mobile device). Also, similar to GUI 1700, GUI 1800 may correspond to a dashboard presentation on the user device. In GUI 1800, instead of an organizational hierarchy view, a user detail view is depicted. It should be understood that the dashboard of GUI 1800 and GUI 1700 may correspond to two different views of the same application. For example, a view selector 1802 of GUI 1800 may allow a user to toggle between an organizational view and a user detail view. In this example, a USP may first select an organizational view (e.g., of a particular facility) in order to see which units may require the most attention. Then, the USP may select the user detail view of the same facility to drill down and identify, for example, individual users within a particular facility (or unit) that may require attention.

Turning to GUI 1800 in further detail, column 1804 may present a USP with options for filtering, similar to column 1702 GUI 1700. In this example, under column 1804, multiple risk levels (e.g., high risk, moderate risk, low risk) are selected. The length of stay (LOS) range is set to 0-5 days. Patients with pressure injuries that were determined to not be POA are included, and users with pressure injuries that were determined to be POA are also included. Other filters may also available within GUI 1800, including, for example, "Division Name" filter 1806, "Facility Name" filter 1808, and "Unit" filter 1810. In this example, the "XYZ Medical Center" facility is selected under the "Facility Name" filter 1808. With this set of filters applied, as depicted in GUI 1800, the number of users in-house is 1 (e.g., see "Patients In-house" indicator 1812, who is also a high-risk user (e.g., see "High Risk Patients" indicator 1814).

A user-level view 1818 may also be displayed within GUI 1800, which may present a list of users and corresponding user data for each user. As depicted, the user-level view 1818 includes user data of one or more users (e.g., displayed in columns) corresponding to: a probability of a pressure injury, the user's name, the admission date/time, the length of stay (LOS), the unit where the user is admitted, the room, age, BMI, sex, etc. The user level view 1818 may also receive a selection (e.g., from a USP) of a particular user, which may then cause the user level view 1818 to display a chart 1816 (e.g., a line chart) that corresponds to the user's risk level over time. In the example depicted in FIG. 18, a user is selected with a probability of 96.21% of having or developing a pressure injury (e.g., a high risk user). The user is checked into the "ICU CARDI" unit. Over the course of time, the chart 1816 reflects that the user's risk level grew from around 43% on October $31^{st}$ to being over 90% on November $1^{st}$. In this case, a USP may thereby determine that this particular user should receive a wound consult, and/or receive specialized service. In some examples, the chart 1816 may reflect a trend for not only a single user, but also multiple users (e.g., an average trend, trends for multiple users overlaid on the same chart, etc.).

It should be understood that one or more queries may be executed for presenting the GUI 1700 of FIG. 17 or GUI 1800 of FIG. 18. In some examples, the queries may be executed by invoking one or more scripts that interact with the prediction system (e.g. the reporting engine 928 of FIG. 9). The queries may be executed on any suitable cadence (e.g., twice a day), either automatically or manually refreshed, and may provide regular updates to a USP of changes in the user(s) condition. Other queries may also be executed to perform regular audits of the prediction model management engine 902 (e.g., via the auditing engine 926 of FIG. 9). In some examples, these audits may be used to determine the performance of a prediction model (e.g., sensitivity, specificity), and may further be used to update one or more parameters of a prediction model (e.g., via the rules engine 930).

Figure 19:
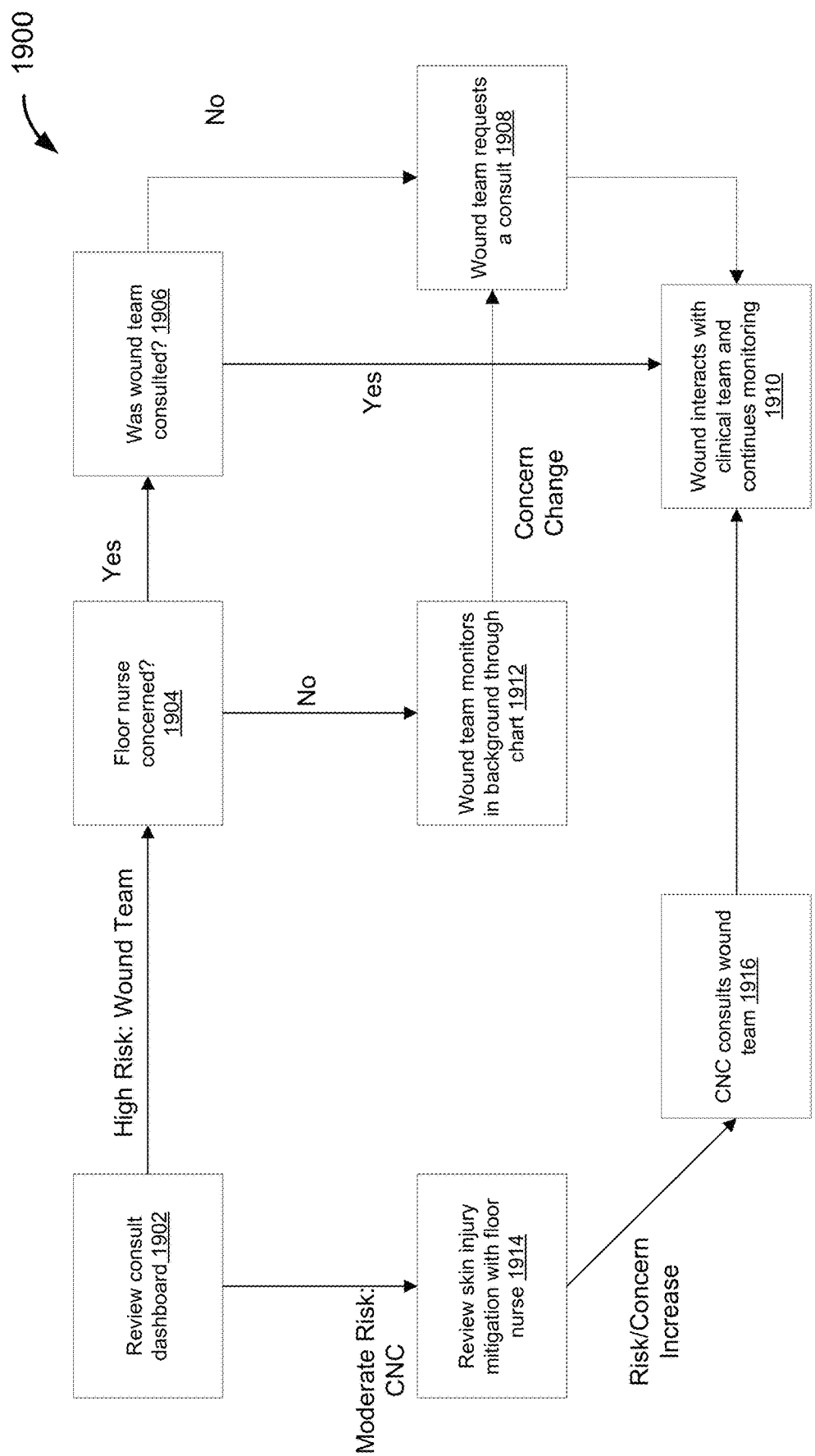
FIG. 19 is an example flowchart illustrating a process for providing a recommendation for servicing a user based on a risk assessment, according to at least one example.

FIG. 19 depicts a simplified a block diagram illustrating a process for utilizing a prediction system (e.g., prediction system 1219) to coordinate user service, in accordance with at least one example. The process may be performed based at least in part on output from a dashboard presentation (e.g., which may be similar to GUI 1700 or GUI 1800) that is generated by the prediction system. For clarity of illustration, in the context of FIG. 19, multiple types of USPs are involved in the process. A clinical nurse consultant (CNC) may be a type of USP that reviews reports from a consult dashboard. A floor nurse may be a type of USP who is a member of the clinical service team and is responsible for managing user service within a portion of a service facility (e.g., the Multi Trauma unit). A wound specialty nurse may be a type of USP who is a member of a wound team. Specialty nurses within the wound team may be tasked with performing consults with users throughout multiple units within a facility, depending on demand for consultation from the various units. Typically, the wound team has a limited number of human resources, and therefore must prioritize users who are at higher risk of having a pressure injury for receiving detailed wound assessments (e.g., or "wound consults"). Meanwhile, the service facility may be responsible for ensuring that each admitted user regularly receives at least a basic skin assessment (e.g., at least once or twice per day). As depicted in FIG. 19 and described herein, a prediction system may be able to automatically generate a skin risk assessment of each admitted user and classify each user has low risk, moderate risk, or high risk. Then, depending on the classification (e.g., moderate risk or high risk), the prediction system may direct one or more USP's to be involved in managing the user's service. In the example depicted in FIG. 19, "high risk" may refer to a risk assessment where the probability of a risk injury (PI) is greater than or equal to 80%. A "moderate risk" may refer to a risk assessment where the probability of a risk injury (PI) is between 50% and 79%. In some cases, by utilizing a prediction system to classify users according to their respective risk levels, the prediction system may capture and provide targeted service for approximately 90% of all actual pressure injuries. This represents a significant improvement over conventional methods at least by enabling scalability and more efficient triaging of users.

At block 1902, a USP (e.g., a CNC) may consult a dashboard. As described above, the dashboard may be similar to GUI 1700 or GUI 1800. The prediction system may determine a classification for a particular user. For example, using GUI 1800 for illustration, the USP may determine that a user within user level view 1818 in the "ICU CARDI" unit is at high risk (96.21%) of having or developing a pressure injury. In this case, the process would proceed to block 1904. In another example, the risk assessment of the prediction system may indicate a moderate risk of a pressure injury, in which case, the process would proceed to block 1914. In the case that the risk assessment indicates a low risk, no further consultation may be recommended.

At block 1904, another USP (e.g., the floor nurse) caring for the particular user may be consulted. For example, the CNC from block 1902 may ask the floor nurse if they have observed any conditions of the user that are concerning, and which may suggest further investigation may be helpful. If yes, the process may proceed to block 1906. If no, the process may proceed to block 1912.

At block 1906, a USP (e.g., the CNC) may assess whether the wound team was already consulted. If no, the process may proceed to block 1908. If yes, the process may proceed to block 1910.

At block 1908, the wound team may request a wound consult with the user based at least in part on the concern reported from the floor nurse. During the wound consult, a wound specialty nurse may assess if a skin wound exists. If so, the specialty nurse may determine what type of wound it is (e.g., including determining the likely root cause), document in clinician notes various aspects of the wound (e.g., length, width, depth, location, stage, tunneling, undermining, wound edges, etc.), and may suggest to the floor nurse recommendations for service.

At block 1910, the wound team may further interact with the clinical team (e.g., the floor nurse), and continue monitoring the user over time. In some cases, this interaction may be further determined based in part on updated dashboard reports (e.g., chart 1816 of FIG. 18).

At block 1912, in the case that the floor nurse was not concerned (at block 1904), the wound team may continue monitoring the user only in the background (e.g., via chart 1816). For example, the nurse may be aware that the user will be shortly discharged, and conclude that a wound consult is not needed. However, in the event that the dashboard indicates an increase in risk (and/or if the floor nurse indicates increased concern), the wound team may step in to request a wound consult with the user.

At block 1914, in the case that the risk assessment for the user indicated only a moderate risk level, the CNC may review skin injury mitigation options with the floor nurse. In this case, instead of proceeding to involve a specialized nurse from the wound team, the floor nurse may only be asked to monitor the user's condition. In some cases, the floor nurse may take mitigating steps to prevent the risk level from escalating.

At block 1916, in the case that the user's risk level increases, the CNC (or other suitable USP) may consult the wound team. In an example, the CNC may review an updated dashboard chart 1816 and determine that the user's risk level has escalated, in which case the CNC asks for the wound team to perform a wound consult for the user.

As mentioned above, this process of generating risk assessments that classifies users according to their risk level allows a more efficient use of human and computing resources, while increasing the total coverage of users at risk of developing pressure injuries (e.g., both high risk and moderate risk).

Figure 20:
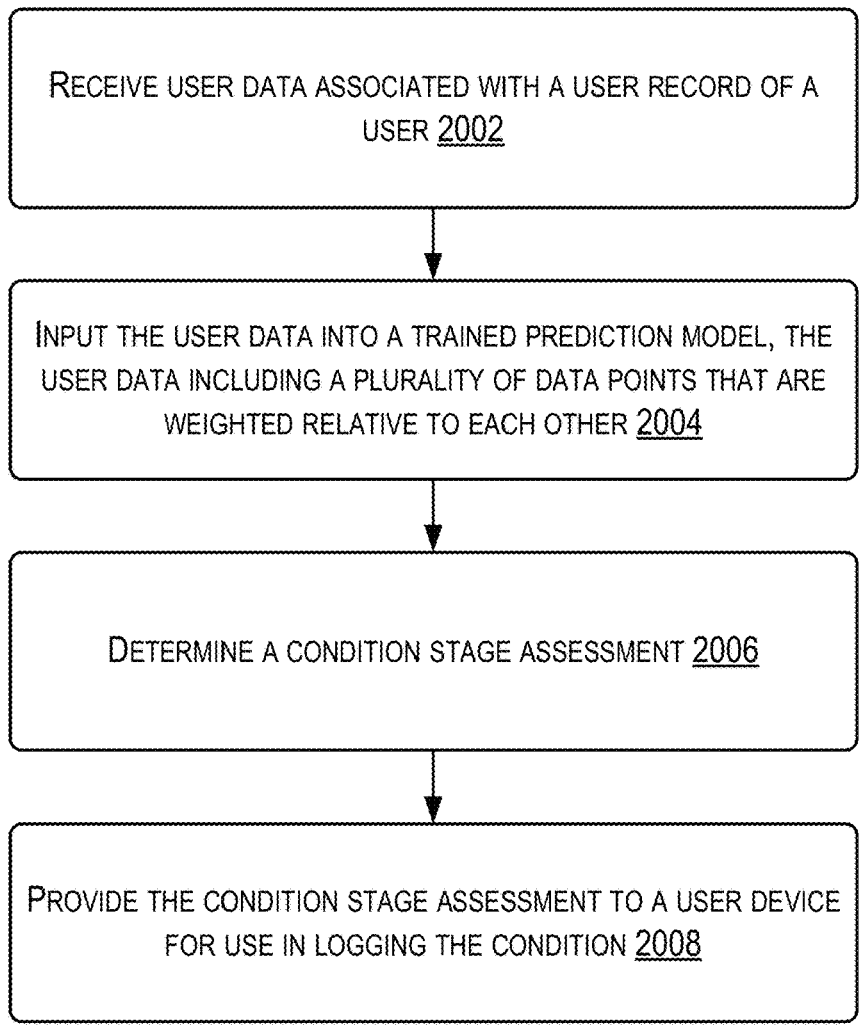
FIG. 20 is an example flow diagram illustrating a process for a prediction system providing a risk assessment for use in coordinating user service, according to at least one example.

FIG. 20 illustrates an example flow diagram illustrating a process 2000 for a prediction system providing a pressure injury stage risk assessment for use in coordinating user service, according to some examples of the present disclosure. In some examples, the prediction system performs the process 2000 (or other processes as described in FIGS. 21-25, variations, and/or combinations thereof) may be similar to prediction system 1219 of FIG. 12.

The process 2000 may start at block 2002, whereby the prediction system may receive user data associated with a user record of a user. In some examples, the operations performed at this block may be similar to the operations described in reference to block 1202 of FIG. 12.

At block 2004, the prediction system may input the user data into a trained prediction model. The user data may include a plurality of data points that are weighted relative to each other. In some examples, the operations performed at this block may be similar to the operations described in reference to block 1204 of FIG. 12. The relative weights (e.g., predictive importance) of the data points may be similar to as described in reference to FIG. 13.

At block 2006, the trained prediction model of the prediction system may determine a condition (e.g., pressure injury) stage risk assessment. In some examples, the operations performed at this block may be similar to the operations described in reference to block 1206 of FIG. 12. In this case, the risk assessment may include at least one of: (1) a prediction (e.g., probability score between 0-1) that the user has a pressure injury at a particular stage, or (2) a prediction that the pressure injury will advance from the particular stage to a next stage within a predetermined time interval (e.g., an average length of stay at the service unit for users with a similar condition). It should be understood that the risk assessment may also include other predictions, as described further herein (e.g., a probability a pressure injury at any stage, a probability of severity based in part on the location of the injury on the body, etc.). In some examples, the trained prediction model may correspond to a type of decision tree model (e.g., a boosted decision tree). The boosted decision tree model may contain a plurality of nodes. A predictive outcome of a node of the plurality of nodes may be determined based at least in part on at least one of: (1) a classifier decision boundary between at least two of the plurality of data points, as described in reference to FIG. 14-16, or (2) the relative weight between at least two of the plurality of data points. In some examples, other techniques may be used to for generating the trained prediction model. For example, one or more neural networks may be used, as described in reference to FIG. 10. For example, a recurrent neural network (RNN) (e.g., Long short-term memory (LSTM)) may be used for determining patterns across time, such as for training the prediction model to predict whether a pressure injury will advance to the next stage, based on previous data. In some examples, any suitable training data may be used to train the prediction model to predict the pressure injury at a particular stage. For example, as described herein, multiple training images may be used to train a neural network to classify pressure injuries according to stages. In some examples, this prediction model may utilize a convolutional neural network (CNN) for image recognition and classification. As described earlier, multiple machine learning models may be used (e.g., as an ensemble) to generate a risk assessment.

At block 2008, the prediction system may provide the condition (e.g., pressure injury) stage risk assessment to a user device. In some examples, the risk assessment may be used by a USP for use in logging the condition (e.g., injury) (e.g., to an affiliated service management system). For example, if the risk assessment determines that the user had a pressure injury at a particular stage upon being admitted, a USP may log the pressure injury as a community-acquired injury. In another example, if the user was admitted with no pressure injury, but then later acquires a pressure injury (e.g., a hospital-acquired pressure injury), the USP may log this information. In other examples, the USP may utilize the risk assessment to determine whether the user should receive a wound consult for the pressure injury.

Figure 21:
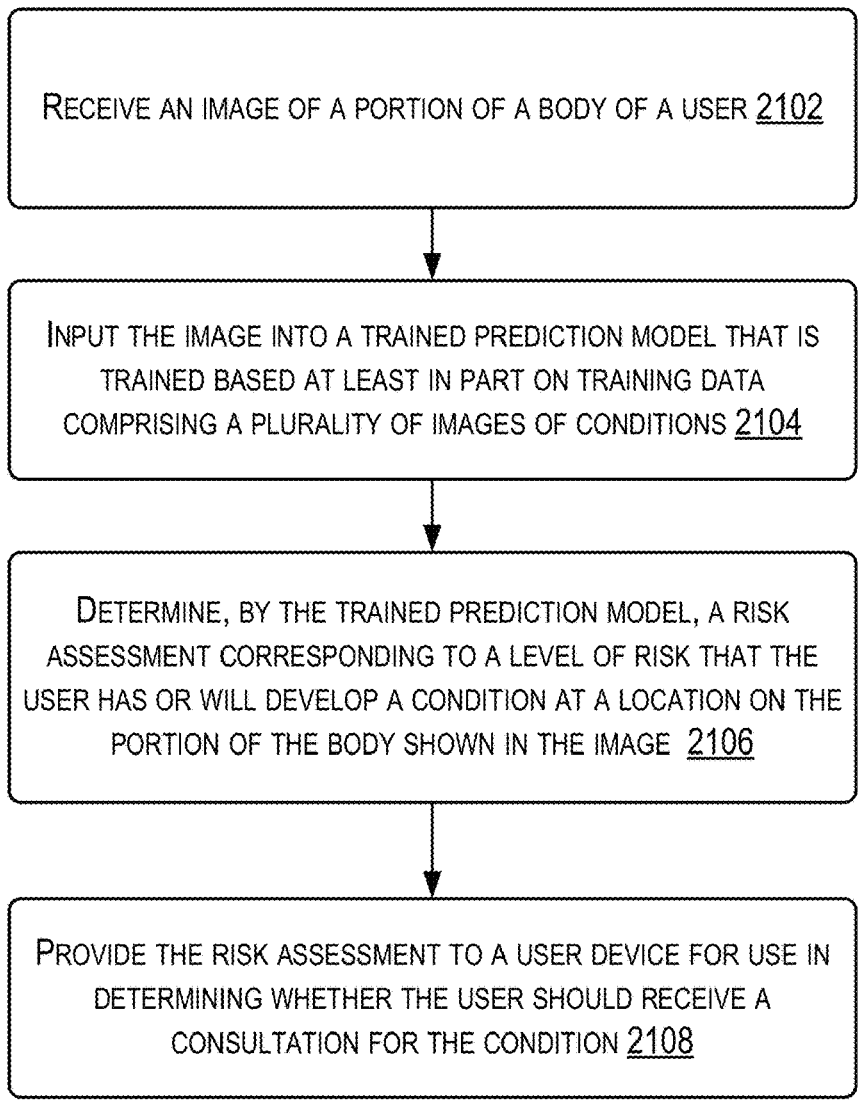
FIG. 21 is an example flow diagram illustrating a process for a prediction system providing a risk assessment for use in coordinating user service, according to at least one example.

FIG. 21 illustrates an example flow diagram illustrating a process 2100 for a prediction system generating a pressure injury risk assessment based at least in part on one or more images of a body of a user, according to some examples of the present disclosure.

The process 2100 may start at block 2102, whereby the prediction system may receive an image of a portion of a body of a user. The image may correspond to an area of the body that may correspond to a particular condition (e.g., presenting a pressure injury (e.g., which may be a latent pressure injury)). In some examples, the image may correspond to one of several elements of user data associated with a user record of the user, similar to as described in reference to block 1202 of FIG. 12. In some examples a plurality of images may be received, for example covering different aspects of the portion of the body, different portions of the body, the same portion over successive time intervals, etc.

At block 2104, the prediction system may input the image into a trained prediction model that is trained based at least in part on training data comprising a plurality of images of conditions on the body (e.g., pressure injuries on the body). In an example, and as described above, the trained prediction model may utilize a neural network (e.g., a CNN or RNN). The prediction model may be trained based on one of several features. For example, the prediction model may identify edges of a potential pressure injury. If the edges of the injury are distinct, then a pressure injury may be involved. Other features may correspond to identifying areas on the body where pressure (or shear) sources may have caused the injury (e.g., boots, oxygen tubs, stockings, strappings, etc.). A large corpus of images may be used to distinguish pressure injuries from, for example, moisture-associated dermatitis, vascular injuries, or other skin tears.

At block 2106, the prediction system may determine, by the trained prediction model, a risk assessment corresponding to a level of risk that the user has or will develop a condition (e.g., a pressure injury) at a location on the portion of the body shown in the image. In some examples, operations at this block may be similar to as described in reference to block 1206 of FIG. 12. In some examples, the image may be used to determine not only the existence of a pressure injury, but a particular stage of the injury, and/or a location on the body of the injury.

At block 2108, the prediction system may provide the risk assessment to a user device for use in determining whether the user should receive a consultation (e.g., a wound consult) for the condition(s) (e.g., the particular pressure injury). In some examples, operations at this block may be similar to as described in reference to block 1208 of FIG. 12.

Figure 22:
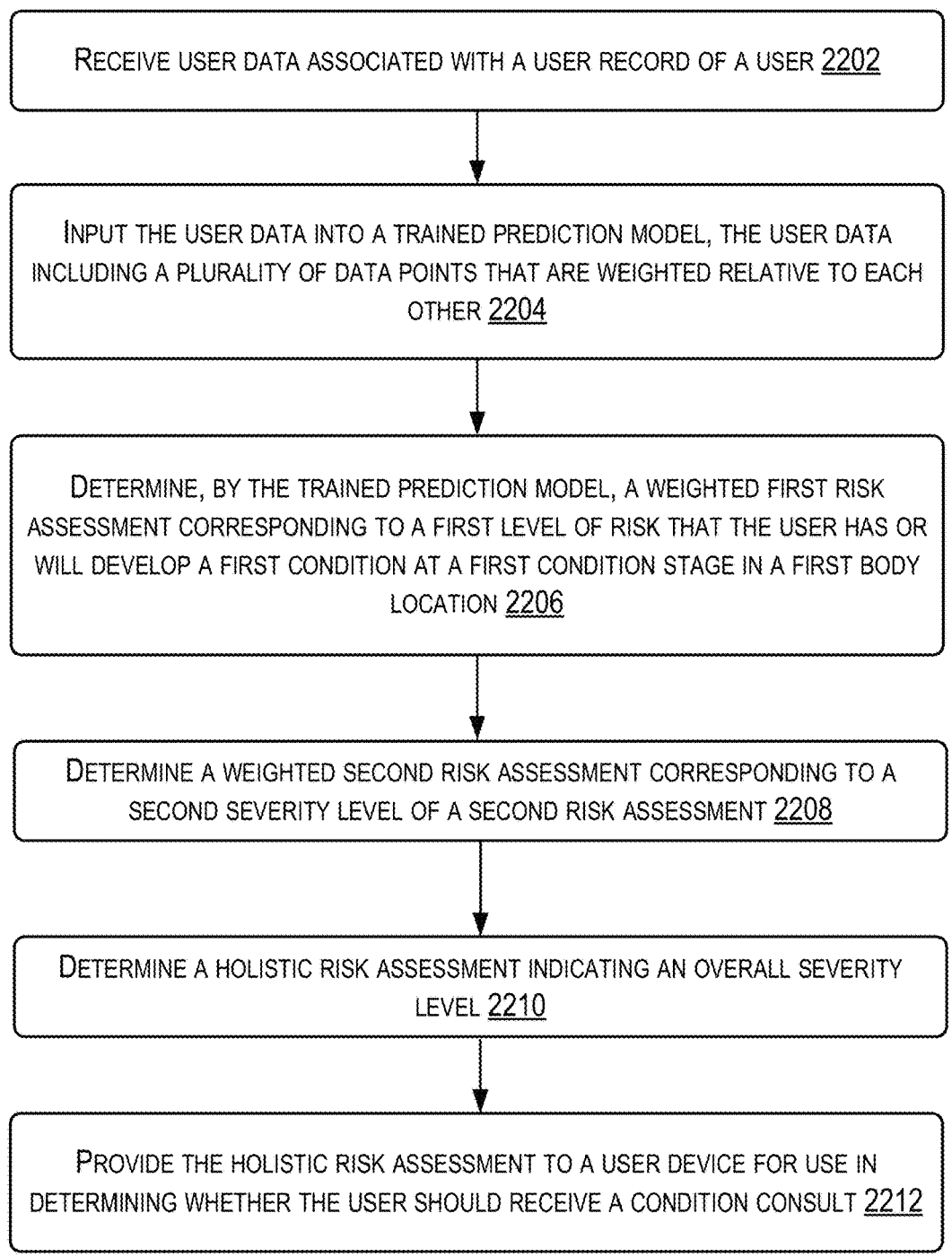
FIG. 22 is an example flow diagram illustrating a process for a prediction system providing a risk assessment for use in coordinating user service, according to at least one example.

FIG. 22 illustrates an example flow diagram illustrating a process 2200 for a prediction system generating a holistic pressure injury risk assessment for use in coordinating user service, according to some examples of the present disclosure.

The process 2200 may start at block 2202, whereby the prediction system may receive user data associated with a user record of a user. In some examples, operations at this block may be similar to as described in reference to block 1202 of FIG. 12.

At block 2204, the prediction system may input the user data into a trained prediction model. In some examples, operations at this block may be similar to as described in reference to block 1204 of FIG. 12.

At block 2206, the prediction system may determine, by the trained prediction model, a weighted first risk assessment corresponding to a first level of risk that the user has or will develop a first condition (e.g., a pressure injury) at a first condition (e.g., injury) stage in a first body location. In some examples, operations at this block may be similar to as described in reference to block 1206 of FIG. 12 and/or block 2006 of FIG. 20. The prediction system may first generate a first risk assessment corresponding to the first level of risk that the user has or will develop the first pressure injury in the first body location. The prediction system may then generate the weighted first risk assessment from the first risk assessment based at least in part on at least one of: (1) the first injury stage (e.g., stage 1, 2, 3 or 4), or (2) the first body location. The weighted first risk assessment may also take into account other factors, including whether the user had previous pressure injuries in that area of the body or pre-existing conditions (e.g., illnesses) that affect that first body location.

At block 2208, the prediction system may determine a weighted second risk assessment corresponding to a second severity level of a second risk assessment. This block may be similar to block 2206, except that is determined in reference to a second pressure injury at a second injury stage in a second body location. It should be understood that the second injury stage of the second pressure injury and the first injury stage of the first pressure injury may be the same or different. In some examples, the second body location and the first body location are in different locations.

At block 2210, the prediction system may determine a holistic risk assessment indicating an overall severity level. The holistic risk assessment may be generated based at least in part on the weighted first risk assessment and the weighted second risk assessment. In some examples, the weighted first risk assessment and the weighted second risk assessment may be combined together, for example, using a weighted scoring algorithm. For example, consider a case where the first risk assessment may be weighted by determining that, although the stage of the injury is 1, the first location is in a sensitive area (e.g., the buttocks) where pressure injuries are known to advance stages more rapidly. For example, the user may be incontinent and may also have a below-average BMI. The second risk assessment may be weighted by determine that, although the second location is not as prone towards injury advancement, the existing pressure injury is already at stage 3. Based on the weighted scores for the respective risk assessments, although each individual risk assessment may not be rated at a high severity level, the prediction system may nevertheless determine that the overall severity level for the user is high.

At block 2212, the prediction system may provide the holistic risk assessment to a user device for use in determining whether the user should receive a condition (e.g., a wound) consult. In some examples, operations at this block may be similar to as described in reference to block 1208 of FIG. 12, and/or FIG. 19.

Figure 23:
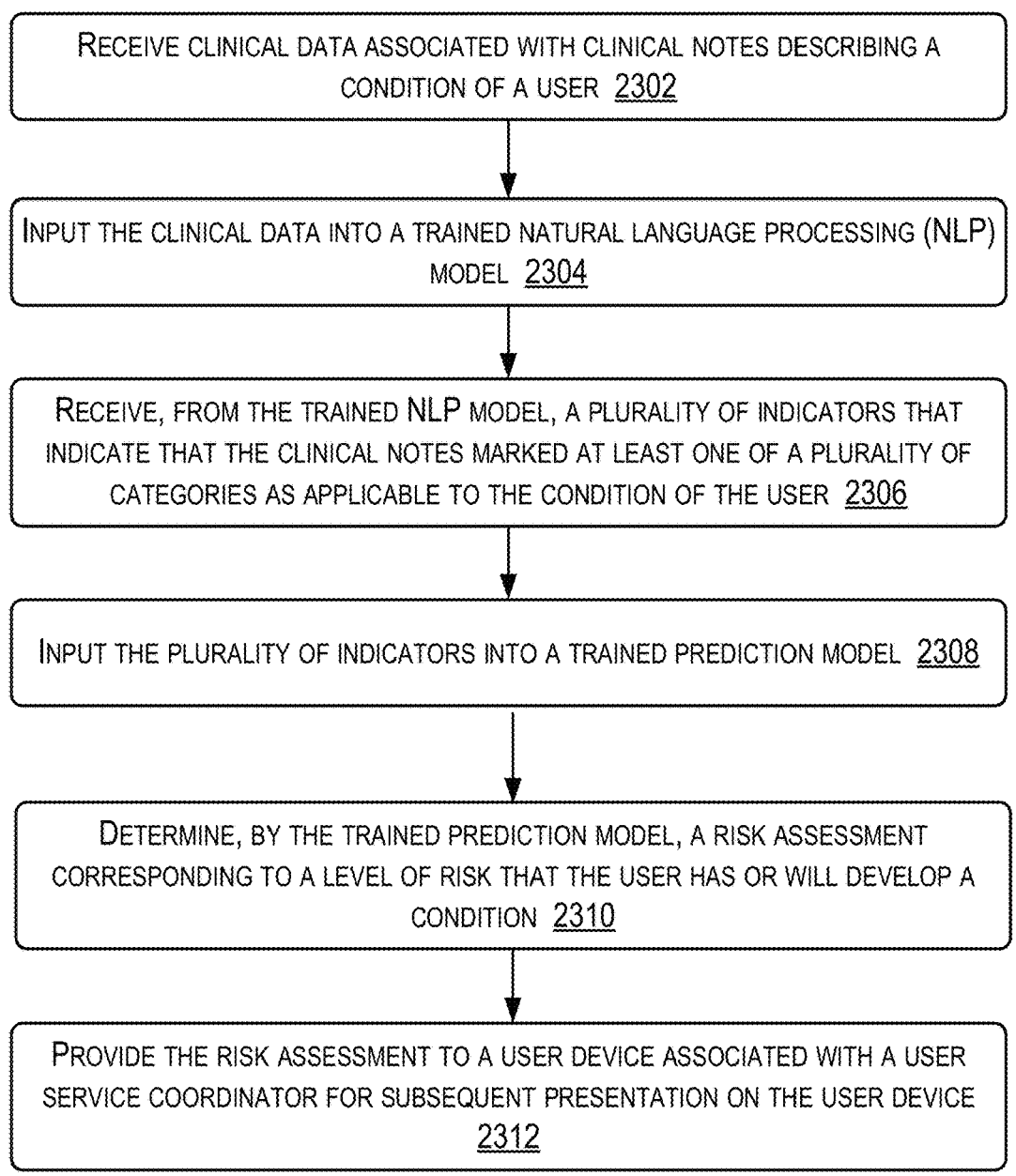
FIG. 23 is an example flow diagram illustrating a process for a prediction system providing a risk assessment for use in coordinating user service, according to at least one example

FIG. 23 illustrates an example flow diagram illustrating a process 2300 for a prediction system generating a pressure injury risk assessment based at least in part on clinician notes, according to some examples of the present disclosure.

The process 2300 may start at block 2302, whereby the prediction system may receive clinical data associated with clinical notes describing a condition of a user. The clinical data described one or more aspects of the user's condition, which may not otherwise be determined based only on blood tests or other automated tests. For example, the notes may describe an overall condition of the user, a location of the wound, a size of the wound, user observations regarding the level of pain they experience, normal living arrangements of the user, etc. The clinical notes may or may not explicitly reference the possibility of a pressure injury within the notes. For example, the notes may be primarily focused on another condition about which the user was admitted, but may indicate details are consistent with a latent pressure injury. In some examples, the clinician notes may correspond to one of several elements of user data associated with a user record of the user, similar to as described in reference to block 1202 of FIG. 12.

At block 2304, the prediction system may input the clinical data into a trained natural language processing (NLP) model. In some examples, the NLP model may utilize a word2vec model (e.g., a continuous bag-of-word (CBOW) model or a skip-gram (SG) model). The word2vec model may be used to learn word embeddings in order to determine semantic meanings of words within the clinician notes. The NLP model may utilize a neural network that is trained and executed similar to as described in reference to FIG. 10 (e.g., based on a corpus of clinicians notes compiled from clinicians throughout the enterprise). It should be understood that the clinical data may be in the form of text, images, video, or other suitable inputs. One or more features may be derived from the data that are suitable for input to the NLP model.

At block 2306, the prediction system may receive, from the trained NLP model, a plurality of indicators that indicate that the clinical notes marked at least one of a plurality of categories as being applicable to the condition of the user. For example, the plurality of categories may be similar to as described in reference to Table 1 and FIG. 13 (e.g., blood quality, body healing indicators, heart quality, etc.). In some examples, an indicator may indicate that one of the data points within one of these categories (e.g., Ambulation) is noted as an issue within the clinician notes for the user's present condition.

At block 2308, the prediction system may input the plurality of indicators into a trained prediction model. In some examples, operations at this block may be similar to as described in reference to block 1204 of FIG. 12.). In some examples, the plurality of indicators may correspond to one of several elements of user data associated with a user record of the user. This may be similar to as described in reference to block 1202 of FIG. 12, and may also include, for example, image data described in reference to FIG. 21). These several elements may be input into the trained prediction model.

At block 2310, the prediction system may determine, by the trained prediction model, a risk assessment corresponding to a level of risk that the user has or will develop a condition (e.g., a pressure injury). This may be similar to as described in reference to block 1206 of FIG. 12.

At block 2312, the prediction system may provide the risk assessment to a user device associated with a user service coordinator for subsequent presentation on the user device. This may be similar to as described in reference to block 1208 of FIG. 12. The risk assessment may be presented on a dashboard of a user device, and may be similar to as described in reference to FIGS. 17 and 18.

Figure 24:
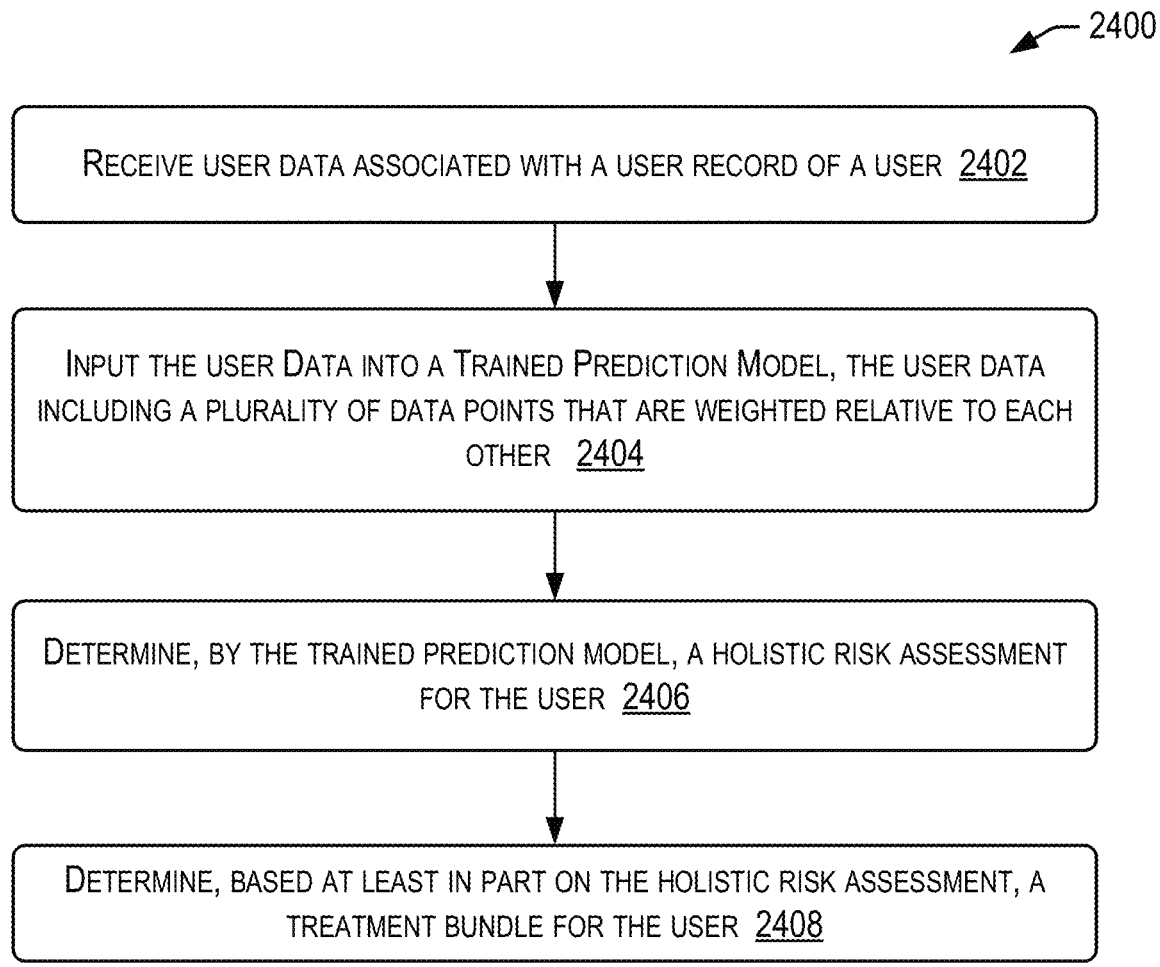
FIG. 24 is an example flow diagram illustrating a process for a prediction system providing a risk assessment for use in coordinating user service, according to at least one example.

FIG. 24 illustrates an example flow diagram illustrating a process 2400 for a prediction system determining a service bundle for a user, according to some examples of the present disclosure.

The process 2400 may start at block 2402, whereby the prediction system may receive user data associated with a user record of a user. In some examples, operations at this block may be similar to as described in reference to block 1202 of FIG. 12.

At block 2404, the prediction system may input the user data into a trained prediction model. In some examples, operations at this block may be similar to as described in reference to block 1204 of FIG. 12.

At block 2406, the prediction system may determine, by the trained prediction model, a holistic risk assessment for the user. In some examples, operations at this block may be similar to as described in reference to block 2210 of FIG. 22.

At block 2408, the prediction system may determine, based at least in part on the holistic risk assessment, a service bundle for the user. In some examples, in addition to training the prediction model based on user training data related to the user's condition, the prediction model may also be trained based at least in part on historical recommendation (or service) and user outcome data. For example, the historical recommendation data may indicate service options that have been recommended and successfully (or unsuccessfully) applied to previous users with pressure injuries. Example service options may include specialized service equipment, instructions for treating (e.g., turning and/or repositioning) the user at a particular frequency, type of medication or service therapy for the user. Example specialized service equipment may include a specialized bed, a pressure visualization system, a wireless sensor monitoring system, sensor socks, custom tubing or masking, foam/padding, etc. Example service therapy may include physical therapy designed to increase mobilization of the user. The prediction model may be trained to recommend service options that are most likely to result in a positive outcome, based in part on historical results. For example, a user may exhibit a pressure injury on their buttocks or hip that is likely caused by incontinence. The pressure injury may be at stage 2. The user may also be allergic to certain types of medication. The prediction model may further determine, based on these parameters, that the particular service bundle should be recommended. The particular service bundle may not include the certain types of medication, but may alternatively include recommendations for a custom bed, regular repositioning of the user every hour, etc. In this way, the prediction system may increase the efficiency of the triage and coordination process, as described in reference to FIG. 19. For example, a CNC or floor nurse may be presented with custom recommendations for treating the user, which may obviate extensive consultations involving the wound team. It should be understood that a particular service bundle determined in part from the holistic risk assessment may be designed to treat illnesses/conditions beyond just the particular one or more pressure injuries. For example, the particular service bundle may indicate a particular medication that is chosen for effectiveness in treating both a pressure injury and another condition of the user.

Figure 25:
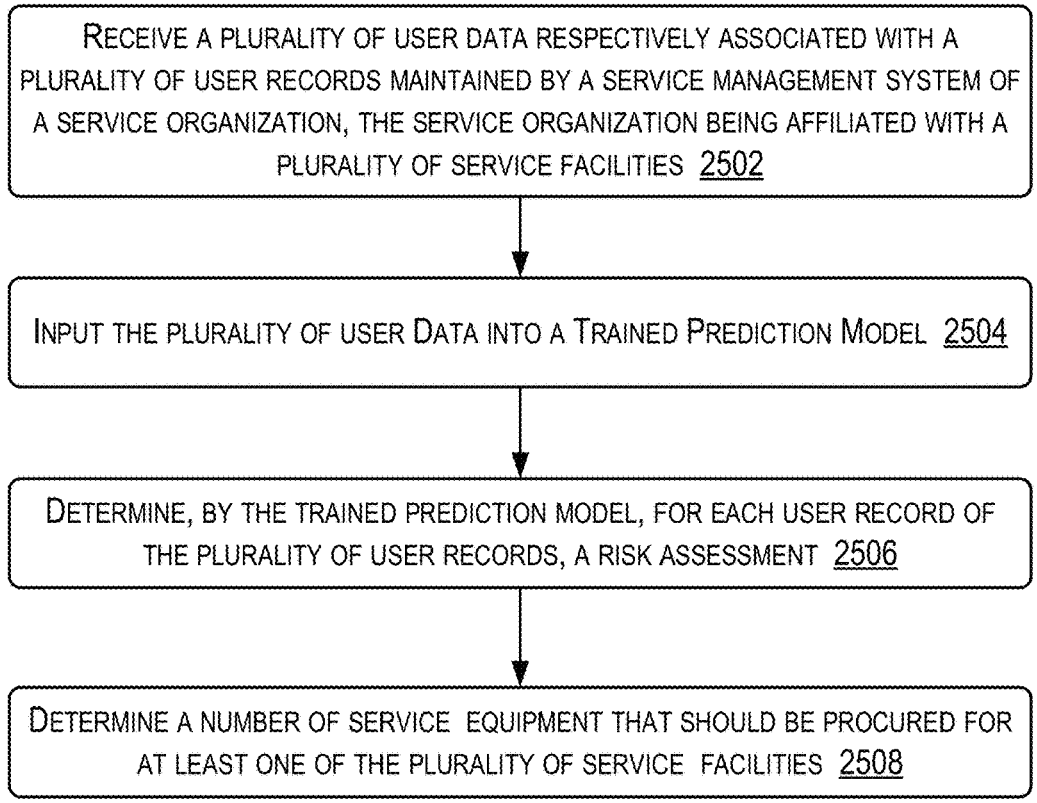
FIG. 25 is an example flow diagram illustrating a process for a prediction system providing a risk assessment for use in coordinating user service, according to at least one example.

FIG. 25 illustrates an example flow diagram illustrating a process 2500 for procuring service equipment based at least in part on using a prediction system to predict pressure injuries, according to some examples of the present disclosure.

The process 2500 may start at block 2502, whereby the prediction system may receive a plurality of user data. The plurality of user data may be respectively associated with a plurality of user records maintained by a service management system of a service organization. The service organization may be affiliated with a plurality of service facilities. The service management system and service organization may be similar to as described herein. In some examples, the user data may be associated with a plurality of admitted users to a particular service facility. The user data may cover a range of time (e.g., a day, a week, a month, a year, etc.).

At block 2504, the prediction system may input the plurality of user data into a trained prediction model. In some examples, operations at this block may be similar to as described in reference to block 1204 of FIG. 12. In some cases, the trained prediction model may also be trained based in part on historical resource utilization data (e.g., a number of service equipment procured over a period of time due to observed pressure injuries and/or previous risk assessments).

At block 2506, the prediction system may determine, by the trained prediction model, for each user record of the plurality of user records, a risk assessment. In some examples, operations at this block may be similar to as described in reference to block 1206 of FIG. 12.

At block 2508, the prediction system may determine a number of service equipment that should be procured for at least one of the plurality of service facilities. For example, the trained prediction model of the prediction system may determine the number of service equipment that should be procured based on the plurality of current risk assessments. Continuing with the example above, the particular service facility may have a number of units, similar to as described in FIGS. 17 and 18, with reference to "XYZ Medical Center." The prediction model may determine that a certain number of custom beds should be procured to meet existing demand. For example, the system may take into account that some users may advance from one injury stage to another injury stage during their time in the service unit. The system may recommend to procure additional equipment to mitigate against and/or properly account for this happening. In some cases, these beds may be transferred between units, loaned from another facility for a period of time, or purchased. By utilizing the prediction system to procure service equipment, examples of the present disclosure may standardize procurement methods across an enterprise. In some cases, the historical resource utilization data may be used by the prediction system to predict future demand, and thereby assist USPs in planning ahead even without current data.

Specific details are given in the above description to provide a thorough understanding of the examples. However, it is understood that the examples may be practiced without these specific details. For example, circuits may be shown in block diagrams in order not to obscure the examples in unnecessary detail. In other instances, well-known circuits, processes, algorithms, structures, and techniques may be shown without unnecessary detail in order to avoid obscuring the examples.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the examples may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, examples may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
receiving, by a pressure-injury prediction system, user data associated with a user record of a user of a service unit, the user record being one of a plurality of user records maintained by a service management system of a service organization, the service unit being one of a plurality of service units affiliated with the service organization;
training a first prediction model using first training data representing first user samples drawn from the service organization;
training a second prediction model using second training data representing second user samples drawn from the service unit;
defining a trained prediction model using the first prediction model and the second prediction model;
inputting, by the pressure-injury prediction system, the user data into the trained prediction model of the pressure-injury prediction system, the user data comprising a plurality of data points that respectively correspond to one of a plurality of categories comprising two or more of: (1) age, (2) body mass index (BMI), (3) blood quality, (4) heart quality, or (5) body healing indicators, the plurality of data points weighted relative to each other by the trained prediction model;
determining, by the trained prediction model, a risk assessment corresponding to a level of risk that the user has or will develop a pressure injury; and
providing, by the pressure-injury prediction system, the risk assessment to a user device of a user service agent for use in determining whether the user should receive a wound consult for the pressure injury.

2. The computer-implemented method of claim 1, wherein defining the trained prediction model further comprises:
receiving, by the pressure-injury prediction system, the first training data comprising the first user samples, a user sample of the first user samples associated with a particular user record maintained by the service management system;
inputting, by the pressure-injury prediction system, the first training data into the first prediction model; and
determining, by the pressure-injury prediction system, a plurality of nodes of a decision tree of the first prediction model based at least in part on the first training data, a predictive outcome of a node of the plurality of nodes determined based at least in part on at least one of: (I) a classifier decision boundary between at least two of the plurality of data points, or (II) a relative weight between at least two of the plurality of data points.

3. The computer-implemented method of claim 1, wherein the level of risk corresponds to at least one of: (I) a prediction that the pressure injury of the user is at a particular stage, or (II) a second prediction that the pressure injury will advance to a second pressure injury within a predetermined time interval.

4. The computer-implemented method of claim 1, wherein the user data includes an image of a portion of a body of the user, and wherein trained prediction model is trained to determine the risk assessment based in part on analyzing the image.

5. The computer-implemented method of claim 4, wherein the risk assessment corresponds to the level of risk that the portion of the body shown in the image has the pressure injury.

6. The computer-implemented method of claim 1, wherein the risk assessment corresponds to the level of risk that the user has or will develop the pressure injury that is associated with at least one of: (I) a particular stage, or (II) a particular location on a body of the user, and wherein the pressure-injury prediction system determines a severity of the pressure injury based at least in part on the particular stage or the particular location on the body.

7. The computer-implemented method of claim 1, further comprising:
receiving, by the trained prediction model, service notes of a service provider user that provides service to the user, the service notes describing the pressure injury of the user; and
performing, by the trained prediction model, natural language processing (NLP) on the service notes, wherein the risk assessment is determined based at least in part the natural language processing of the service notes.

8. The computer-implemented method of claim 1, wherein determining the risk assessment comprise determining the risk assessment based at least in part on combining a first risk assessment of the first prediction model with a second risk assessment of the second prediction model.

9. A pressure-injury prediction system, comprising:
a memory configured to store computer-executable instructions; and
a processor configured to access the memory and execute the computer-executable instructions to at least:
receive user data associated with a user record of a user of a service unit, the user record being one of a plurality of user records maintained by a service management system of a service organization, the service unit being one of a plurality of service units affiliated with the service organization;
train a first prediction model using first training data representing first user samples drawn from the service organization;
train a second prediction model using second training data representing second user samples drawn from the service unit;
define a trained prediction model using the first prediction model and the second prediction model;
input the user data into the trained prediction model, the user data comprising a plurality of data points that respectively correspond to one of a plurality of categories, the plurality of data points weighted relative to each other by the trained prediction model;
determine a risk assessment corresponding to a level of risk that the user has or will develop a pressure injury; and
provide the risk assessment to a user device of a user service agent for use in determining whether the user should receive a wound consult for the pressure injury.

10. The system of claim 9, wherein defining the trained prediction model further comprises:
receiving the second training data comprising the second user samples, a user sample of the second user samples associated with a particular user record maintained by the service management system;
inputting the second training data into the second prediction model; and determining a plurality of nodes of a decision tree of the second prediction model based at least in part on the second training data, a predictive outcome of a node of the plurality of nodes determined based at least in part on at least one of: (I) a classifier decision boundary between at least two of the plurality of data points, or (II) a relative weight between at least two of the plurality of data points.

11. The system of claim 9, wherein the level of risk corresponds to at least one of: (I) a prediction that the pressure injury of the user is at a particular stage, or (II) a second prediction that the pressure injury will advance to a second pressure injury within a predetermined time interval.

12. The system of claim 9, further comprising additional instructions that, when executed by the system, cause system to perform additional operations comprising:
determining a service bundle for the user that corresponds to at least one of: (I) a type of equipment to be used for servicing the user, (II) a type of service for the user, or (III) a frequency of service for the user.

13. The system of claim 9, further comprising additional instructions that, when executed by the system, cause system to perform additional operations comprising:
determining that a type of equipment will be procured for the service unit based at least in part on the risk assessment.

14. The system of claim 9, wherein the risk assessment corresponds to a level of risk that a particular portion of a body of the user is associated with the pressure injury.

15. The system of claim 9, wherein the risk assessment corresponds to the level of risk that the user has or will develop the pressure injury that is associated with at least one of: (I) a particular stage, or (II) a particular location on a body of the user, and wherein the system determines a severity of the pressure injury based at least in part on the particular stage or the particular location on the body.

16. One or more non-transitory computer-readable storage devices comprising computer-executable instructions that, when executed by one or more computer systems, cause the one or more computer systems to perform operations, comprising:
receiving user data associated with a user record of a user of a service unit, the user record being one of a plurality of user records maintained by a service management system of a service organization, the service unit being one of a plurality of service units affiliated with the service organization;
training a first prediction model using first training data representing first user samples drawn from the service organization;
training a second prediction model using second training data representing second user samples drawn from the service unit;
defining a trained prediction model using the first prediction model and the second prediction model;
inputting the user data into the trained prediction model, the user data comprising a plurality of data points that respectively correspond to one of a plurality of categories, the plurality of data points weighted relative to each other by the trained prediction model;
determining a risk assessment corresponding to a level of risk that the user has or will develop a pressure injury; and
providing the risk assessment to a user device of a user service agent for use in determining whether the user should receive a consultwound consult for the pressure injury.

17. The one or more non-transitory computer-readable storage devices of claim 16, wherein the level of risk corresponds to at least one of: (I) a prediction that the pressure injury of the user is at a particular stage, or (II) a second prediction that the pressure injury will advance to a second pressure injury within a predetermined time interval.

18. The one or more non-transitory computer-readable storage devices of claim 16, wherein the risk assessment corresponds to the level of risk that the user has or will develop the pressure injury that is associated with at least one of: (I) a particular stage, or (II) a particular location on a body of the user, and wherein the instructions further comprise determining a severity of the pressure injury based at least in part on the particular stage or the particular location on the body.

19. The one or more non-transitory computer-readable storage devices of claim 16, wherein the trained prediction model comprises the first prediction model and the second prediction model, and wherein defining the trained prediction model further comprises:
receiving the first user samples of the training data, a user sample of the first user samples associated with a particular user record maintained by the service management system;
training the first prediction model using the first user samples, wherein a predictive outcome of a node of a plurality of nodes of a decision tree is determined based at least in part on at least one of: (I) a classifier decision boundary between at least two of the plurality of data points, or (II) a relative weight between at least two of the plurality of data points;
receiving the second user samples of the training data, the second user samples corresponding to a subset of the first user samples; and
training the second prediction model using the second user samples, wherein the risk assessment is determined based at least in part on combining a first risk assessment of the first prediction model with a second risk assessment of the second prediction model.

20. The one or more non-transitory computer-readable storage devices of claim 16, further comprising additional instructions that, when executed by the one or more computer systems, cause the one or more computer systems to perform additional operations comprising:
receiving service notes of a service provider user that provides service to the user, the service notes describing the pressure injury of the user; and
performing natural language processing (NLP) on the service notes, wherein the risk assessment is determined based at least in part the natural language processing of the service notes.

* * * * *